United States Patent
Nishino et al.

[11] Patent Number: 6,001,880
[45] Date of Patent: Dec. 14, 1999

[54] ALKYLENEDIAMINE DERIVATIVE, ANTI-ULCER DRUG, AND ANTIBACTERIAL DRUG

[75] Inventors: Chikao Nishino, Kanagawa; Tomohiro Uetake; Nao Kojima, both of Tokyo; Hirotada Fukunishi; Fumitaka Sato, both of Kanagawa, all of Japan

[73] Assignee: Shiseido Co., Ltd., Tokyo, Japan

[21] Appl. No.: 09/053,667

[22] Filed: Apr. 2, 1998

[30] Foreign Application Priority Data

Apr. 4, 1997 [JP] Japan ................... 9-102631

[51] Int. Cl.⁶ .................. A01N 37/18; C07C 233/74
[52] U.S. Cl. .................. 514/617; 514/618; 514/619; 564/162; 564/163; 564/183
[58] Field of Search .................. 564/183, 162, 564/163; 514/617, 618, 619

[56] References Cited

FOREIGN PATENT DOCUMENTS

| | | |
|---|---|---|
| 0183190 | 11/1985 | European Pat. Off. . |
| 0735031 | 10/1996 | European Pat. Off. . |
| 1458953 | 11/1966 | France . |
| 1542708 | 10/1968 | France . |
| 2245619 | 4/1975 | France . |
| 2352791 | 12/1977 | France . |
| 2452478 | 10/1980 | France . |
| 2160871 | 1/1986 | United Kingdom . |

OTHER PUBLICATIONS

CA 70:37496, Palazzo et al., 1969.
CA 87: 67997, Takashi et al., 1977.
CA 85: 116918, 1976.
H. Yoshida Chemical Abstracts, vol. III, No. 25, Dec. 18, 1989.
Y. Kase Chemical Abstracts, vol. 72, No. 25, Jun. 22, 1970.
R.A. Gupta Chemical Abstracts, vol. 110, No. 17, Apr. 24, 1989.
T.G. Karevina Chemical Abstracts, vol. 109, No. 11, Sep. 12, 1988.
G.B. Glavin Chemical Abstracts, vol. 107, No. 19, Nov. 9, 1987.
M.S. Manekar Chemical Abstracts, vol. 101, No. 17, Oct. 22, 1984.
I. Monkovic Chemical Abstracts, vol. 109, No. 7, Aug. 15, 1988.

*Primary Examiner*—Jane Fan
*Attorney, Agent, or Firm*—Snider & Chao, LLP; Fei-Fei Chao; Ronald R. Snider

[57] ABSTRACT

An alkylenediamine derivative or a salt thereof expressed by the following formula 1:

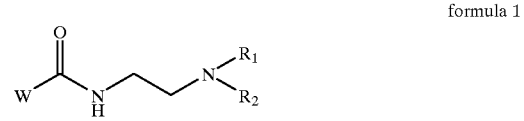

formula 1 wherein each of $R_1$ and $R_2$ represents a lower alkyl group, and W represents a group expressed by any of the following formulas 2 and 3;

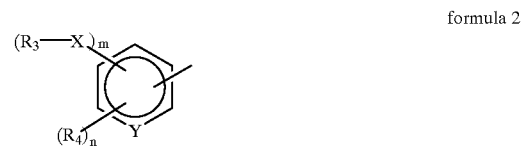

formula 2

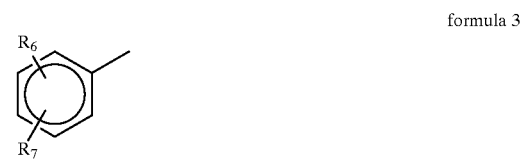

formula 3

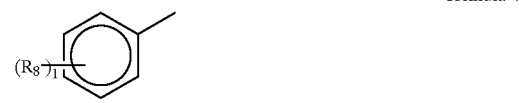

formula 4 wherein all variables are as defined in the specification

The alkylenediamine derivative has an anti-ulcer effect or an antibacterial activity against *Helicobacter pyroli*, and has also high safety to be available for prevention or cure of ulcers.

38 Claims, 3 Drawing Sheets

REACTION FORMULA A;

REACTION FORMULA B;

REACTION FORMULA C;

REACTION FORMULA D:

REACTION FORMULA E:

REACTION FORMULA F:

ALKYLENEDIAMINE DERIVATIVE, ANTI-ULCER DRUG, AND ANTIBACTERIAL DRUG

RELATED APPLICATIONS

This application claims the priority of Japanese Patent Application No. 9-102631 filed on Apr. 4, 1997, which is incorporated herein by reference.

FIELD OF THE INVENTION

The present invention relates to an alkylenediamine derivative and, in particular, to an alkylenediamine derivative having an antibacterial activity against *Helicobacter pyroli* or an anti- ulcer effect.

BACKGROUND OF THE INVENTION

Various theories have been proposed with respect to a cause of ulcer in human. In particular, it has been elucidated that stress, taking of non-steroidal anti-inflammatory drugs for curing rheumatic diseases, and the like are closely related to ulcer formation, mainly due to relatively excess gastric or duodenal acid secretion. Accordingly, it is important to suppress the acid secretion in order to prevent ulcer formation and to cure it.

On the other hand, it has been considered that *Helicobacter pyroli*, which is a rod normally existing in stomach, generates ammonia due to its strong urease activity, thereby inducing ulcer. Since it persistently lives within mucus and mucosa, it becomes the greatest cause for recurrence of ulcer. Accordingly, it has been considered that the recurrence of ulcer can be prevented if this bacterium is sterilized.

Though various kinds of medicaments for curing ulcer have been conventionally developed, few medicaments have been known to have an effect for preventing stress ulcers from generating or an antibacterial activity against *Helicobacter pyroli*.

DISCLOSURE OF THE INVENTION

The present invention has been performed in view of the problems of the above-mentioned prior art and its object is to provide a compound which is excellent in preventing ulcer from generating and to provide antibacterial drug against *Helicobacter pyroli* and anti-ulcer drug including such a compound as a main component.

As a result of the diligent studies conducted by the inventors for the object, it has been found that a specific alkylenediamine derivative is effective against various kinds of ulcer due to its antibacterial property against *Helicobacter pyroli* or its acid secretion inhibition as a main action mechanism. Thus, the present invention has been accomplished.

Namely, an alkylenediamine derivative or a salt thereof in accordance with the present invention is expressed by the following formula 1:

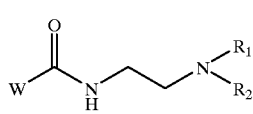

(I)

formula 1 wherein each of $R_1$ and $R_2$ represents a lower alkyl group, and W represents a group expressed by any of the following formulas 2 to 4;

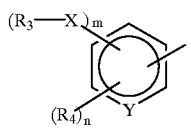

formula 2

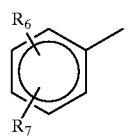

formula 3

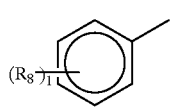

formula 4 wherein $R_3$ is an alkenyl group;
  $R_4$ is a lower alkyl group, a lower alkoxy group, or a halogen atom;
  X is a group expressed by —O—, —S—, or —N($R_5$)—, while $R_5$ is hydrogen atom, a lower alkyl group, or an alkenyl group;
  Y is carbon or nitrogen atom;
  m is an integer of 1 to 3;
  n is an integer of 0 to 2;
  $R_6$ is a lower alkyl group;
  $R_7$ is hydroxy or benzyloxy group;
  $R_8$ is a lower alkyl, a lower alkoxy, a piperidinoalkyl, a substituted carbamoyl, or a substituted amino group; and
  1 to 1 or 2.

An anti-ulcer drug in accordance with the present invention comprises, as an effective ingredient, said alkylenediamine derivative or the pharmacologically acceptable salt thereof, together with a pharmaceutically acceptable carrier and/or adjuvant.

An antibacterial drug against *Helicobacter pyroli* in accordance with the present invention comprises, as an effective ingredient, said alkylenediamine derivative or the pharmacologically acceptable salt thereof, together with a pharmaceutically acceptable carrier and/or adjuvant.

A method for the treatment of peptic ulcers in man or mammals in accordance with the present invention comprises administering an effective amount of said alkylenediamine derivative or the pharmacologically acceptable salt thereof to a host.

A method for the inhibition of acid secretion in stomach of man or mammals in accordance with the present invention comprises administering an effective amount of said alkylenediamine derivative or the pharmacologically acceptable salt thereof to a host.

A method for the inhibition of growth of *Helicobacter pyroli* in stomach of man or mammals in accordance with the present invention comprises administering an effective amount of said alkylenediamine derivative or the pharmacologically acceptable salt thereof to a host.

A method for the prevention of peptic ulcers in man or mammals in accordance with the present invention comprises administering an effective amount of said alkylenediamine derivative or the pharmacologically acceptable salt thereof to a host.

EXAMPLES

Figure 1:
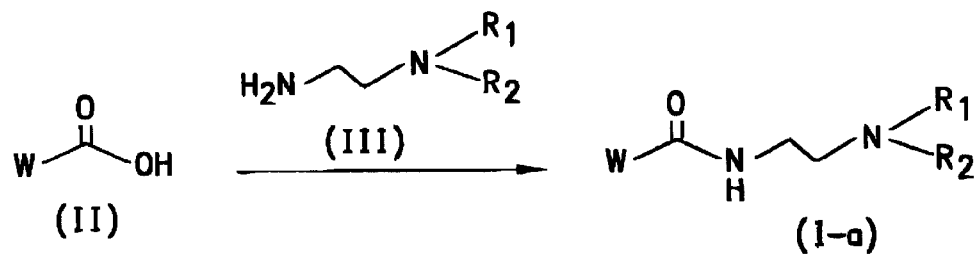
FIGS. 1 and 5 show examples of steps for manufacturing the alkylenediamine derivatives in accordance with the present invention and FIGS. 2 to 4 and FIGS. 6 to 8 show examples of steps for manufacturing material compounds for the alkylenediamine derivative in accordance with the present invention.

In the compound in accordance with the present invention, the lower alkyl group found at $R_1$ and $R_2$ is a straight or branched alkyl group having 1 to 8 carbon atoms. Examples thereof include methyl, ethyl, n-propyl, n-butyl, isopropyl, isobutyl, 1-methylpropyl, tert-butyl, n-pentyl, 1-ethylpropyl, isoamyl, n-hexyl, and n-octyl group. While each of $R_1$ and $R_2$ may be identical to or different from each other, it is preferable they are identical to each other from the viewpoint of easiness of acquisition or manufacture. A preferable example of $R_1$ and $R_2$ is methyl, ethyl, or isopropyl group from the viewpoint of effect. Particularly, ethyl or isopropyl group is preferable.

The alkenyl group found at $R_2$ represents a straight or branched alkenyl group which has at least one double bond and has 2 to 20 carbon atoms. While the double bond has two kinds of configurations, namely, cis and trans, each double bond in alkenyl group may have either configurations. Among such alkenyl groups, a preferable example thereof is a branched alkenyl group. Particularly, prenyl, geranyl, neryl or farnesyl is preferable.

In the compound of the present invention, $R_4$ represents a lower alkyl group, lower alkoxy group, or halogen atom. While the lower alkyl group is defined as that above, it is preferably isobutyl group. The lower alkoxy group represents an alkoxy group derived from the lower alkyl group mentioned above. A preferable example of the lower alkoxy group is methoxy group. Examples of halogen atom include fluorine, chlorine, bromine, and iodine. A preferable example of halogen is fluorine.

In the compound of the present invention, X represents a group expressed by —O—, —S—, or —N($R_5$)—. Here, $R_5$ represents hydrogen, a lower alkyl, or an alkenyl group, while the lower alkyl and alkenyl group are defined as those above. A preferable example of X is —O—.

While the lower alkyl group found at $R_6$ is defined as that above, it is preferably isobutyl group.

$R_7$ represents hydroxy or benzyloxy group. The benzyloxy group can have halogen atom on its benzene ring as a substituent. A preferable example of such halogen atom is fluorine.

The lower alkyl group and alkenyl group found at $R_8$ are defined as that above. Here, when $R_8$ is a lower alkoxy group and n is 2, for example, the two alkoxy group may form a heterocycle such as methylenedioxy group in Example 58 mentioned below.

The alkyl group of "piperidinoalkyl group" found at $R_8$ is examplified by the above-mentioned lower alkyl group. A preferable example of piperidinoalkyl group is piperidinomethyl group.

The substituted carbamoyl group found at $R_8$ is preferably carbamoyl group having at least one substituent. An example of such a substituent is a lower alkyl group. Here, the lower alkyl group is defined as that above, and is preferably tert-butyl group.

The substituted amino group found at $R_8$ is preferably amino group having at least one substituent. Examples of such a substituent include a lower alkyl and lower acyl group. Here, the lower alkyl group is defined as that above. The lower acyl group represents the acyl group derived from the lower alkyl group mentioned above. A preferable example of the lower acyl group is pivaloyl group.

A preferable compound of the present invention may be expressed by the following formula 5:

formula 5

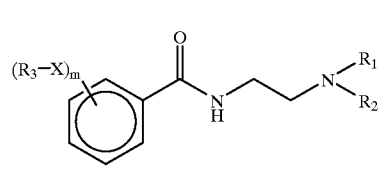

wherein $R_1$, $R_2$, $R_3$, X and m are same as those in the above-mentioned formula 1.

A preferable compound of the present invention may be expressed by the following formula 6:

formula 6

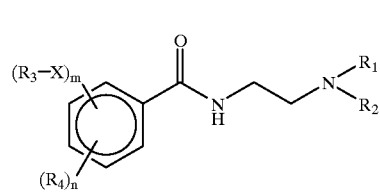

wherein $R_1$, $R_2$, $R_3$, $R_4$, X and m are same as those in the above-mentioned formula 1; and n is 1 or 2.

In formula 6, it is preferable that $R_4$ is a lower alkoxy group.

A preferable compound of the present invention may be expressed by the following formula 7:

formula 7

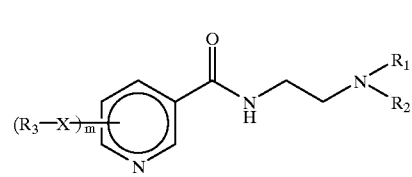

wherein $R_1$, $R_2$, $R_3$, X and m are same as those in the above-mentioned formula 1.

In formula 7, m is preferably 1.

In formula 1, 5, 6, or 7, it is preferable that $R_3$ is prenyl, geranyl, neryl or farnesyl group.

In formula 1, 5, 6, or 7, X is preferably —O—.

A preferable compound of the present invention may be expressed by the following formula 8:

formula 8

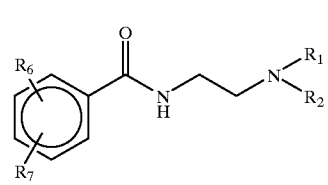

wherein $R_1$, $R_2$, $R_6$, and $R_7$ are same as those in the above-mentioned formula 1.

In formula 8, $R_6$ is preferably isobutyl group.

In formula 1, 5, 6, 7 or 8, it is preferable that $R_1$ and $R_2$ are ethyl or isopropyl groups.

A preferable compound of the present invention may be expressed by the following formula 9:

formula 9

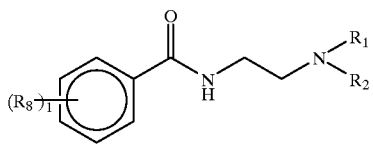

wherein $R_1$, $R_2$, $R_8$ and 1 are same as those in the above-mentioned formula 1.

In formula 9, it is preferable that $R_8$ is a lower alkyl or a lower alkoxy group.

In formula 9, it is preferable that $R_8$ is a piperidinoalkyl or a substituted carbamoyl group and that 1 is 1.

In formula 9, it is preferable that $R_8$ is a substituted amino group and that 1 is 1.

In formula 9, it is preferable that $R_1$ and $R_2$ are isopropyl groups.

In the following, while the general method for manufacturing the compound of the present invention will be explained, it should not be restricted thereto.

Among the compound (I) of the present invention expressed by formula 1, the compound(I-a) in which W is a group expressed by formula 2 or 4 can be manufactured by reaction formula A shown in FIG. 1.

In reaction formula A, the alkylenediamine derivative(I-a) of the present invention can be obtained from a carboxylic acid(II) and an amine(III) by using a known amide-bond forming reaction such as mixed anhydride method, acid chloride method, DCC method, CDI method, or azide method. Here, in reaction formula A, $R_1$ and $R_2$ are defined as those of formula 1 mentioned above.

In the mixed anhydride method, by using an activator such as diphenyl phosphinic chloride, ethyl, chloroformate, isobutyl chloroformate, or pivaloyl chloride, the carboxylic acid (II) is converted into its corresponding anhydride and then reacted with the amine(III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of $-15°$ C. to the reflux temperature of the solvent.

In the acid chloride method, as an activator, for example, phosphorus pentachloride, phosphorus trichloride, or thionyl chloride is used to convert the carboxylic acid (II) into the corresponding acid chloride and then the latter is reacted with the amine(III). As an additive, for example, an organic base such as triethyl amine, pyridine, or N-methylmorpholine can be used. As a solvent, for example, a halogenated hydrocarbon such as dichloromethane or chloroform; an aromatic hydrocarbon such as benzene, toluene, or xylene; or an amide such as dimethyl formamide or dimethylacetamide can be used. While the reaction temperature and reaction time may be changed according to the material compounds used, the reaction is usually effected at a temperature within the range of $0°$ C. to the reflux temperature of the solvent.

In the DCC method, as a condensing agent, for example, dicyclohexyl carbodiimide (DCC) or 1-ethyl-3-(3-dimethylaminopropyl)carbodiimide hydrochloride (WSCI) can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. If necessary, this reaction may be effected while 1-hydroxybenzotriazole (HOBt) or N-hydroxy succinimide (HOSu) is added thereto. While the reaction temperature and reaction time may be changed according to the material compounds used, the reaction is usually effected at a temperature within the range of $0°$ C. to the reflux temperature of the solvent.

In the CDI method, as an activator, for example, N, N'-carbonyldiimidazole is used to convert the carboxylic acid (II) into the corresponding N-acyl derivative and then the latter is reacted with the amine(III). As an additive, for example, an organic base such as triethylamine, pyridine, or N-methylmorpholine or an inorganic base such as sodium hydride or potassium hydride can be used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of $0°$ C. to the reflux temperature of the solvent.

In the azide method, as an activator, for example, diphenylphosphorylazide is used to convert the carboxylic acid (II) into the corresponding azide and then the latter is reacted with amine(III). As an additive, for example, an organic base such as triethylamine, pyridine, or N-methylmorpholine is used. As a solvent, for example, a halogenated hydrocarbon such as dichloromethane or chloroform; an aromatic hydrocarbon such as benzene, toluene, or xylene; an ether such as tetrahydrofuran or dioxane; or an amide such as dimethylformamide or dimethylacetamide can be used. While the reaction temperature and reaction time may be changed according to the material compounds used, the reaction is usually effected at a temperature within the range of $0°$ C. to the reflux temperature of the solvent.

Specifically, for example, diphenylphosphinic chloride or pivaloyl chloride is used as an activator for the mixed anhydride method, while triethylamine is used as an additive to effect a reaction in a solvent such as chloroform or dimethyl formamide at a temperature within the range of $-15°$ C. to room temperature, thereby attaining the aimed object.

Figure 2:
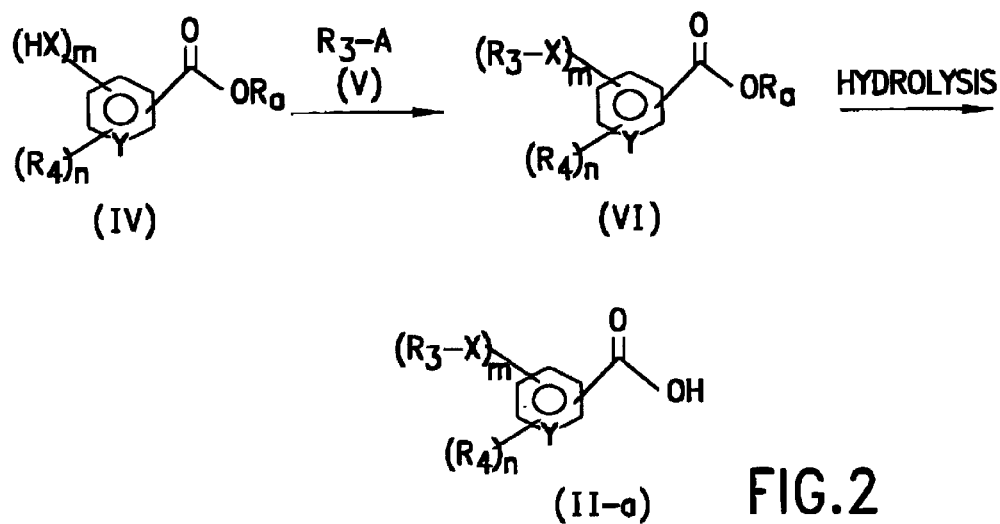

Among the material compounds(II) used in reaction formula A, the compound (II-a) in which W is a group expressed by formula 2 can be synthesized according to reaction formula B shown in FIG. 2, for example. In reaction formula B, $R_3$, $R_4$, X, Y, m, and n are defined as those of formula 2. Ra represents a carboxyl-protecting group which may be a lower alkyl group such as methyl group, ethyl group, or tert-butyl group, phenacyl group, or trichloroethyl group as long as no problem occurs in the subsequent reaction. A represents a halogen atom. In the following, Ra and A are similar to those above as long as there is no description.

In reaction formula B, an alkenyl halide(V) is reacted with a compound(IV) in the presence of a base and then hydrolyzed so as to synthesize the carboxylic acid (II-a).

The first step of this reaction can be effected in the presence of a base. Sodium amide, triethylamine, sodium hydride, sodium hydroxide, potassium carbonate, barium oxide, silver oxide, or the like can be used therefor. Also, a catalytic amount of potassium iodide can be added thereto. As a solvent, for example, an alcohol such as methanol, ethanol, or butanol; an aromatic compound such as benzene, toluene, xylene, or pyridine; an ether such as diethylether, tetrahydrofuran, or dioxane; an amide such as dimethylformamide or dimethylacetamide; or a ketone such as dimethylsulfoxide or acetone can be used. While the reaction temperature and reaction time may be changed according to the material compounds used, the reaction is usually effected at a temperature within the range of 0° C. to the reflux temperature of the solvent.

Specifically, for example, the compound (IV) is dissolved in tetrahydrofuran or N,N'-dimethylformamide and, after sodium hydride is added as a base and stirred therein, the alkenyl halide(V) is added thereto so as to effect a reaction at a temperature within the range of room temperature to the reflux temperature of the solvent, thereby attaining the aimed object.

In the reaction of the second step, the compound (VI) is hydrolyzed in the presence of an acid or a base so as to synthesize the carboxylic acid (II-a). Hydrochloric acid, sulfuric acid, p-toluenesulfonic acid, or the like can be used as the acid, while sodium hydroxide, potassium hydroxide, potassium t-butoxide, or the like can be used as a base. As a solvent, a carboxylic acid such as formic acid or acetic acid, an alcohol such as methanol or ethanol; water; or a mixed solvent thereof can be used. While the reaction temperature and reaction time can be changed according to the material compounds used, the reaction is usually effected at a temperature within the range of 0° C. to the reflux temperature of the solvent.

Specifically, for example, the compound(VI) is dissolved in an alcohol such as methanol or ethanol and then an aqueous sodium hydroxide or potassium hydroxide solution is added thereto so as to effect a reaction at a temperature within the range of room temperature to reflux temperature of the solvent, thereby attaining the aimed object.

By using this reaction formula B, among the material compounds(II) of reaction formula A, a compound in which W is a group expressed by formula 4 and $R_8$ is an alkoxy group can be synthesized.

Figure 3:
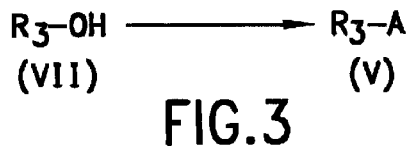

The material compound (V) used in reaction formula B can be synthesized according to reaction formula C shown in FIG. 3. In reaction formula C, $R_3$ is defined as that of reaction formula B mentioned above.

In this reaction formula, the alkenyl halide (V) can be obtained by halogenation of alcohol (VII).

For this reaction, a general method known as halogenation of hydroxy groups can be used. As a reagent of halogenation, for example, a strong acid such as hydrochloric acid or hydrobromic acid; a phosphorus compound such as phosphorus tribromide, phosphorus trichloride, or phosphorus pentachloride; thionyl chloride; N-halogenosuccinimide and dimethyl sulfide; triphenylphosphine and a halogenated hydrocarbon; or methanesulfonyl chloride and lithium halide is used to effect the reaction. As a solvent, for example, a halogenated hydrocarbon such as dichloromethane or chloroform; an aromatic compound such as benzene, toluene, xylene, or pyridine; an ether such as diethylether, tetrahydrofuran or dioxane; or an amide such as N,N-dimethylformamide or N,N-dimethylacetamide can be used. While the reaction temperature and reaction time may be changed according to the material compounds used, the reaction is usually effected at a temperature within the range of 0° C. to the reflux temperature of the solvent.

Specifically, for example, in the presence of lithium chloride and triethylamine, methanesulfonyl chloride is used so as to effect a reaction in a solvent such as acetone at a temperature within the range of 0° C. to room temperature, thereby attaining the aimed object.

Figure 4:
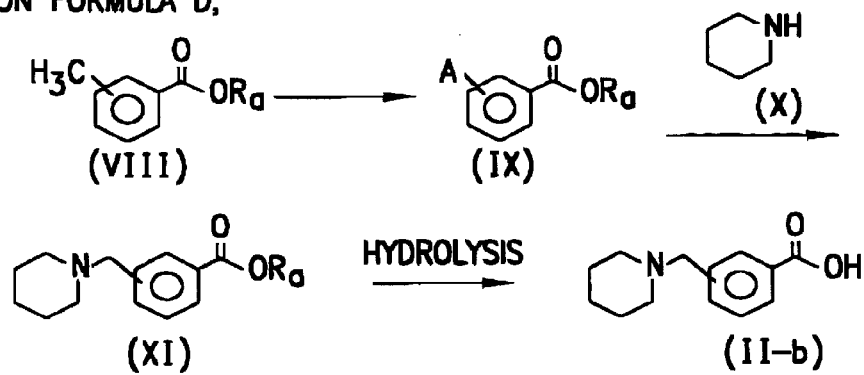

Among material compounds (II) used in reaction formula A, the compound (II-b) in which W is a group expressed by formula 4 mentioned above and $R_8$ is piperidinoalkyl group can be synthesized according to reaction formula D shown in FIG. 4, for example.

At the first step of reaction formula D, a benzyl halide(IX) is obtained by halogenation of the methyl group of the compound (VIII). As a reagent for this reaction, for example, N-bromosuccinimide(NBS), N-chlorosuccinimide(NCS), N-halogenocaprolactam, 1,3-dihalogeno-5,5-dimethlhydantoin, or the like can be used. As a solvent, for example, a halogenated hydrocarbon such as dichloromethane or chloroform; an aromatic compound such as benzene, toluene, xylene, or pyridine; an ether such as tetrahydrofuran or dioxane; or an amide such as N,N-dimethylformamide or N,N-dimethylacetamide can be used. If necessary, this reaction may be effected while a peroxide such as benzoyl peroxide is added thereto. While the reaction temperature and reaction time may be changed according to the material compounds used, the reaction is usually effected at a temperature within the range of 0° C. to the reflux temperature of the solvent.

Specifically, for example, the compound(VIII) is dissolved in dichloromethane, and in the presence of a catalyst N-bromosuccinimide is added to the solution so as to effect a reaction at the reflux temperature of the solvent, thereby attaining the aimed object.

At the second step of reaction formula D, the piperidine (X) is reacted with the benzyl halide(IX) in the presence of a base to obtain the compound (XI). This reaction can be effected under the condition similar to that of the first step in reaction formula B.

At the third step of reaction formula D, the carboxylic acid (II-b) can be obtained by hydrolysis of the compound (XI). This reaction can be effected under the condition similar to that of the second step in reaction formula B.

Figure 5:
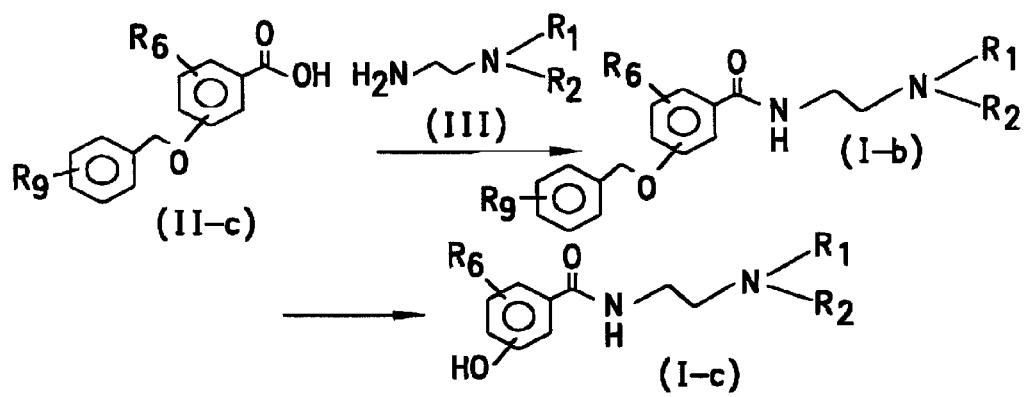

On the other hand, among the compounds(I) of the present invention, the compound in which W is a group expressed by formula 3 can be obtained according to reaction formula E shown in FIG. 5. Namely, the compound(I-b), in which W is a group expressed by formula 3 and $R_7$ is benzyloxycarbonyl group, can be synthesized from a carboxylic acid (II-c) and an amine (III) by using the condensation method described in reaction formula A. Also, by debenzylation of the compound (I-b), the compound (I-c) of the present invention, in which W is formula 3 and $R_7$ is hydroxy group, can be obtained. In reaction formula E, $R_1$, $R_2$, and $R_6$ are defined as those of formula 1. $R_9$ represents hydrogen or halogen atom. In the following, $R_9$ is similar to that above as long as there is no description.

For this debenzylation, various kinds of known methods can be used. For example, reductive elimination method or acid elimination method can be used. Specifically, for example, under catalytic reduction condition, by using palladium-carbon as a catalyst, a reaction is effected in a solvent such as ethanol at a temperature within the range of room temperature to the reflux temperature of the solvent, thereby attaining the aimed object.

Figure 6:
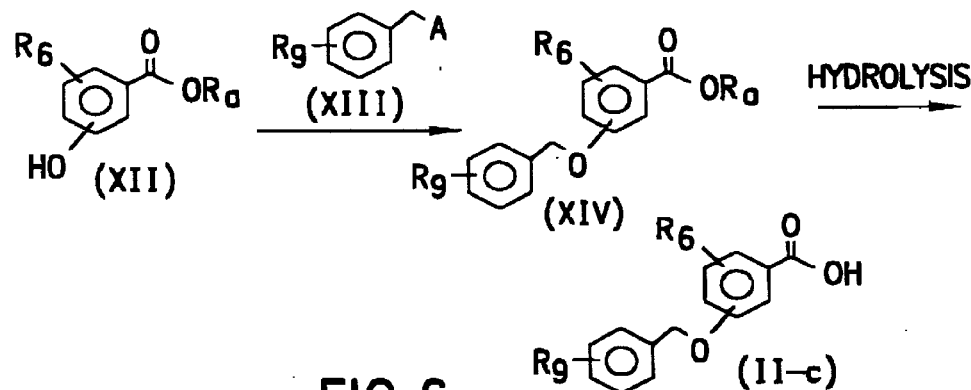

The material compound (II-c) used in reaction formula E can be synthesized according to reaction formula F shown in FIG. 6, for example.

At the first step of reaction formula F, the compound (XII) is reacted with the benzyl halide(XIII) in the presence of a base so as to obtain the compound (XIV). As a base in this reaction, for example, an inorganic base such as potassium carbonate, potassium hydroxide, sodium hydroxide, or sodium hydride; or an organic base such as triethylamine or pyridine can be used. Specifically, for example, potassium carbonate is used as a base so as to effect a reaction in a solvent such as acetone or N,N-dimethylformamide at a temperature within the range of room temperature to the reflux temperature of the solvent, thereby attaining the aimed object.

At the second step of reaction formula F, the compound (XIV) is hydrolyzed so as to obtain the carboxylic acid(II-c). This reaction can be effected under the condition similar to that of the second step in reaction formula B.

Figure 7:
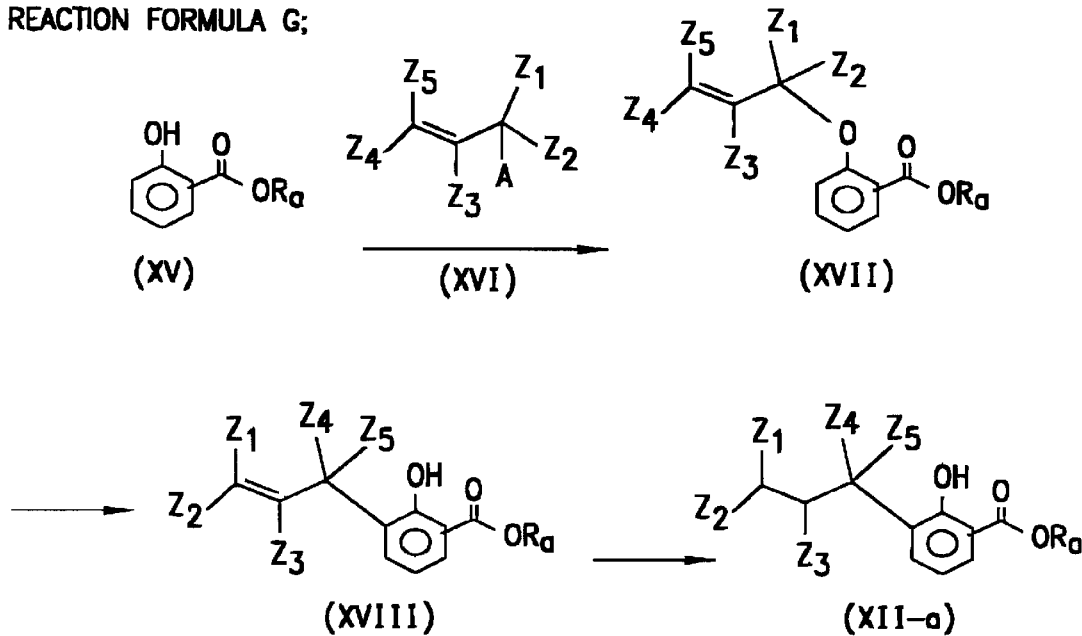

The material compound(XII) used in reaction formula F may be commercially available or easily synthesized by using a known method. For example, the compound (XII-a) can be manufactured according to reaction formula G shown in FIG. 7. In reaction formula G, each of $Z_1$, $Z_2$, $Z_3$, $Z_4$, and $Z_5$ represents hydrogen atom or a lower alkyl group.

At the first step of reaction formula G, the compound(XV) is reacted with the alkenyl halide (XVI) in the presence of a base so as to obtain the compound (XVII). As a base in this reaction, for example, an inorganic base such as potassium carbonate, potassium hydroxide, sodium hydroxide, or sodium hydride, or an organic base such as triethylamine or pyridine can be used. Specifically, for example, potassium carbonate is used as a base so as to effect a reaction in a solvent such as acetone or N,N-dimethylformamide at a temperature within the range of room temperature to the reflux temperature of the solvent, thereby attaining the aimed object.

At the second step of reaction formula G, the compound (XVII) is subjected to Claisen rearrangement reaction so as to obtain the compound(XVIII). This reaction is effected in or without the presence of a high-boiling solvent under normal or high pressure. Examples of the high-boiling solvent include phenyl ether and N,N-dimethylaniline. While the reaction temperature and reaction time may be changed according to the material compounds used, the reaction is normally effected at a temperature within the range of 100 to 200° C.

At the third step of reaction formula G, the compound (XII-a) can be obtained by hydrogenation of the compound (XVIII). When this reaction is effected under a catalytic reduction condition, as a catalyst, palladium, platinum, nickel, rhodium, ruthenium, or the like can be used. Specifically, for example, by using palladium-carbon, in a solvent such as ethanol, ethyl acetate, or tetrahydrofuran, under a hydrogen gas atmosphere, a reaction is effected at a temperature within the range of room temperature to the reflux temperature of the solvent, thereby attaining the aimed object.

Figure 8:
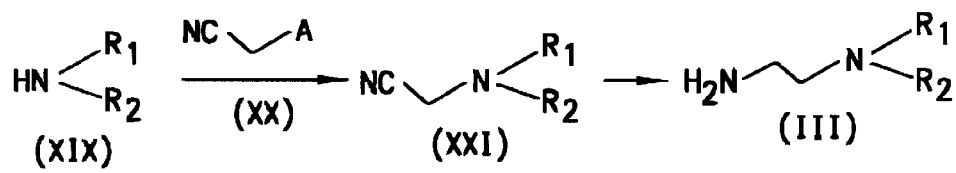

On the other hand, the material compound (III) used in reaction formula A, for example, can be synthesized according to reaction formula H shown in FIG. 8.

In reaction formula H, a halogenoacetonitrile (XX) is reacted with an amine (XIX) in the presence of a base and then the cyano group is reduced so as to synthesize the amine (III). Here, in reaction formula H, $R_1$ and $R_2$ are defined as those of formula 1.

At the first step of this reaction, the reaction can be effected under a reaction condition similar to that of the first step in reaction formula B.

For reduction of the cyano group at the second step in this reaction, a known method can be used. For example, Birch reduction method, a reduction method by a metal hydride complex compound, or a method using Raney nickel can be used. In Birch reduction, while sodium or lithium is used mainly as a catalyst, the reaction can be effected in the mixed solvent of liquid ammonia and an alcohol such as methanol or ethanol. When the metal hydride complex compound is used, lithium aluminium hydride, aluminium hydride, sodium borohydride, or the like can be used as a reagent. As a solvent, for example, an ether such as diethylether, tetrahydrofuran or dioxane; or an alcohol such as methanol, ethanol, or butanol can be used. When sodium borohydride is used, Raney nickel, aluminium chloride, cobalt chloride, or the like can be used as a catalyst. When Raney nickel is used, methanol saturated by ammonia is used as a solvent so as to effect hydrogenation under a pressure, thereby attaining the aimed object. While the reaction temperature and reaction time may be changed according to the material compounds used in all cases, the reaction is usually effected at a temperature within the range of 0° C. to the reflux temperature of the solvent.

Specifically, the example, lithium aluminium hydride is suspended in tetrahydrofuran while being cooled with ice and, after the compound (XXI) is dropped thereto, the reaction is effected at a temperature within the range of 0° C. to the reflux temperature of the solvent. Then, the reaction solution is treated with water, an aqueous sodium hydroxide solution, or the like, thereby attaining the aimed object.

Among the material compounds used in the above-mentioned reaction formulas, those with no preparation methods described may be commercially available or easily synthesized by using a known method.

Also, examples of salts of the alkylenediamine derivative of the present invention (I) with an acid include salts with inorganic acids such as hydrochloric acid, hydrobromic acid, sulfuric acid, or phosphoric acid and salts with organic acids such as acetic acid, propionic acid, citric acid, lactic acid, oxalic acid, maleic acid, fumaric acid, succinic acid, tartaric acid, or methane sulfonic acid. These salts can be easily manufactured by a normal method.

The alkylenediamine derivative in accordance with the present invention has a strong effect against stress ulcer and an excellent effect for suppressing gastric acid secretion. Further, it has an antibacterial activity against *Helicobacter pyroli* which is supposed to be a cause for recurrence of ulcer. Furthermore, it has a high safety. Accordingly, it is useful as a medicament for curing and preventing peptic ulcer in man or mammals and, particularly, gastric ulcer in man. Conventionally, there has hardly been known such a compound which has both effect for suppressing gastric acid secretion and antibacterial activity against *Helicobacter pyroli*. Accordingly, it is indicated that the compound of the present invention is not only effective in preventing and curing ulcer but also in preventing the recurrence thereof.

When the compound of the present invention is administered as a medicament for curing and preventing peptic ulcer, it may be administered orally as tablet, powder, granule, capsule, syrup, or the like as well as parenterally as suppository, injection, external drug, instillation or the like. While the amount of administration may be outside of the range mentioned below according to the degree of symptom, personal difference, age, kind of ulcer, or the like, it should of course be adjusted so as to fit the individual circumstances in specific cases. Usually 0.01 to 200 mg/kg or, preferably, 0.05 to 50 mg/kg or, more preferably, 0.1 to 10 mg/kg is administered per day for an adult in a single dose or several doses.

When formulating the medicament, a normal manufacturing method is used with a normal formulation carrier. If necessary, pharmacologically and pharmaceutically acceptable additives may be added thereto.

Namely, when preparing an oral solid formulation, after an excipient and, if necessary, a binder, a decaying agent, a luster, a coloring agent, a correctives, and the like are added to the main medicament, a normal method is used to form tablet, coated tablet, granule, powder, capsule, or the like.

Examples of the excipient include lactose, corn starch, sucrose, glucose, sorbitol, crystalline cellulose, and silicon dioxide. Examples of the binder include polyvinylalcohol, polyvinylether, ethyl cellulose, methyl cellulose, gum arabic, tragacanth, gelatin, shellac, hydroxypropyl cellulose, hydroxypropyl starch, and polyvinylpyrrolidone. Examples of the decaying agent include starch, agar, gelatin powder, crystalline cellulose, calcium carbonate, sodium hydrogencarbonate, calcium citrate, dextrin, and pectin. Examples of the luster include magnesium stearate, talc, polyethyleneglycol, silica, and hardened vegetable oil. As the coloring agent, those permitted to be added to medicines are used. Examples of the correctives include cocoa powder, menthol, aromatic acid, mentha oil, borneol, and cinnamon powder. If necessary, these tablet and granule can be coated with sugar-coating, gelatin-coating, and the like.

When preparing an injection, if necessary, a pH-adjusting agent, a buffer, a stabilizer, a solubilizer, and the like are added to the main medicament and then a normal method is used to form subcutaneous, intramuscular, and intravenous injection drugs.

In the following, the present invention will be explained in further detail by specifically examples. However, the present invention should not be restricted to these examples.

First, test methods used for evaluating these examples will be explained.

WIS: Restraint and Water Immersion Stress-Induced Ulcer Inhibition Test i) Meaning The degree of inhibition of the stress ulcer formation is tested.

ii) Method

Male Crj:SD or Slc:SD rats (6 to 7-week-old) were fasted overnight, but allowed free access to water. Each group has 5 to 8 of these rats. The sample compound was dissolved or suspended in an aqueous solution of 0.3% sodium carboxymethylcellulose or 0.05% Tween 80 and then was orally administered (100 mg/10 ml/kg). To a control group, the vehicle was administered. 10 minutes later, the rats were placed in a stress cage and immersed to the level of xipfoid process in a water bath (21° C.) for 7 hours. At the end of the stress, the rats were sacrificed by inhalation of ether or carbon dioxide. Then, the stomach of each was removed, inflated by injecting 10 ml of 5% formalin neutral buffer solution, and immersed in 1% formalin neutral buffer solution for 30 minutes or more to be fixed. The stomach was incised along the greater curvature and then the length of each erosion in the glandular portion was determined under dissecting microscope. The sum of the length of erosions per stomach was defined as ulcer index (UI).

iii) Judgment Standard

The effect obtained when 100 mg/kg of the sample compound had been administered was expressed as ulcer formation inhibitory rate (%) as follows:

ulcer formation inhibitory rate (%)=(1-(UI in sample group/UI in control group))×100

CAP: Acid Secretion Inhibition Test In Vitro i) Meaning

The acid secretion inhibitory activity in a cell level is studied. It can also be used for studying the mechanism of the effect.

ii) Method ii-a) Preparation of isolated gastric fundus gland suspension

First, an isolated gastric fundic gland sample was prepared. Namely, a male Japanese White rabbit (2.5 to 3 kg) was anesthetized to death with Nembutal™ and then the abdomen was incised. Immediately thereafter, the stomach was removed and, after its pyloric and cardiac antrum were severed, incised along its greater curvature into two sheets. The gastric contents adhering to the mucosal surface was washed out with ice-cooled PBS (−) and then carefully washed therein. The gastric wall was spread on a cork board with its mucosal surface facing up and the feed and mucus thereon were completely removed with sterile gauze. The mucosa was separated therefrom by a spatula and then collected in ice-cooled PBS (−). After being washed twice with PBS (−), the mucosa was minced into 2–3 $mm^3$ pieces by scissors. These pieces were further washed twice with a nutrient solution. The nutrient solution comprises 132.4 mM of NaCl, 5.4 mM of KCl, 5 mM of $Na_2HPO_4 \cdot 12H_2O$, 1 mM of $NaH_2PO_4 \cdot 2H_2O$, 1.2 mM of $MgSO_4$, 1 mM of $CaCl_2$, 25 mM of HEPES, 2 mg/ml of glucose, and 1 mg/ml of BSA.

Into 70 ml of the nutrient solution containing 1 mg/ml of collagenase, minced mucosal pieces were dispersed and intensely stirred in a conical flask with a stirrer at 37° C. for 40 to 60 minutes. During this period, 100% $O_2$ was sprayed on the nutrient solution surface and the pH was appropriately measured such that it was immediately adjusted to pH 7.4, when the value was therebelow, with a base. The nutrient solution was added to the reaction solution so as to attain the total amount of about 200 ml. After being filtered through a mesh, the suspension was divisionally introduced into 50 ml centrifuge tubes and left for 15 minutes such that gastric fundic gland was deposited. The supernatant was repeatedly removed by an aspirator, dispersed in the nutrient solution, and then left such that the gastric fundic gland was washed three times. At this time, without using a pipette, the suspension was alternately introduced into two centrifuge tubes so as to effect dispersion. The number of cells was counted under microscope and adjusted to $1.6 \times 10^6$ cells/ml.

ii-b) [$^{14}$C]-aminopyrine uptake test

Then, [$^{14}$C]-aminopyrine uptake test was performed. After an Eppendorf tube was weighed, 10 μl (final concentration: $10^{-5}$M) of histamine dissolved in the above-mentioned nutrient solution, 10 μl (final concentration: $10^{-3}$ 5M) of the test compound dissolved in DMSO, and 10 μl (final concentration: 0.05 μCi/ml) of [$^{14}$C]-aminopyrine diluted with the nutrient solution were introduced therein and then 970 μl of the isolated gastric fundic gland suspension prepared above was added thereto. Subsequently, this mixture was shaken at 37° C. for 40 minutes at 125 cycles/minute. After being centrifuged for 30 seconds, 200 μl of its supernatant was collected into a mini-vial, while the rest was removed by an aspirator. The gland pellet was completely dried as the tube with its lid being opened was kept for one night in a drying oven at 80° C. and then the lid was closed and the weight was determined at room temperature. Then 100 μl of 1N KOH was added thereto and the tube with its lid being closed was treated at 60° C. for 1 to 2 hours so as to dissolve the pellet. Then, the contents thereof were transferred to a mini-vial. Into the mini-vial containing the supernatant or gland pellet, 4 ml of Atomlite™ was added and then the radioactivity was measured by a liquid scintillation counter. Here, after the radioactivity of the gland pellet was corrected by using a sample in which 20 mM of NaSCN was added so as to cancel the hydrogen ion concentration gradient, the integration ratio of aminopyrine specifically trapped by the gland pellet was calculated. This experiment was performed in duplicate.

ii-c) Calculation of the accumulation rate of aminopyrine

Here, its principle will be briefly explained. In the isolated gastric fundic gland, acid is accumulated in a space between its secretory tubule and intraglandular cavity. Aminopyrine is weak base (pKa=5.0) and nonionic in a neutral solution so as to freely pass through the cell membrane, whereas it is ionized in an acidic solution and thus cannot pass through the cell membrane due to its electric charge. Therefore, aminopyrine is accumulated in a closed acidic space within the isolated gastric fundic gland. In view of this characteristic, the accumulation rate (R) of aminopyrine is calculated by the following equation:

R=((corrected radioactivity of precipitate)/(radioactivity of supernatant))×(200/(mg dry weight of gland pellet))

iii)Judgment Standard

The effect of the sample compound at the final concentration of $10^{-5}$ M was expressed by acid secretion inhibitory rate (%) as follows:

acid secretion inhibitory rate (%)=(1-(R in sample group/R in control group))×100

AHP: Antibacterial Activity Test Against *Helicobacter pyroli* i)Meaning

The minimum inhibitory concentration (MIC) against *Helicobacter pyroli* (microacrophilic gram-negative bacterium which is supposed to deeply involve in pathogenesis, relapse, and recrudescence of ulcer, referred to as "HP" in the following) is measured so as to find out compounds which have antibacterial activity against *Helicobacter pyroli*.

ii)Method

MICs were determined by the agar dilution method. The stock culture (−80° C.) of HP NCTC 11637 was thawed and cultured on tripticase soy agar supplemented with 5% sheep blood at 37° C. in an atmosphere of 5% $O_2$, 10% $CO_2$, and 85% $N_2$. Grown colonies were transferred to the same plate and precultured for 3 days under the same condition.

A 1,000 µg/ml solution of the sample compound containing DMSO not more than 25% was diluted with sterile purified water so as to have various kind of concentrations. 100 µl volume from each dilution was mixed thoroughly with 900 µl of brucella agar supplemented with 5% horse blood and solidified in a 24 well micro plate, thereby yielding an MIC measurement plate.

An appropriate amount of the colony grown on the plate by preculturing was suspended in Mueller Hinton broth till turbidness was recognizable by naked eyes, thereby yielding a bacterial suspension concentrate containing about $10^7$ cfu/ml. This bacterial suspension concentrate was diluted 100-fold in the same broth; this resulted in a bacterial suspension for inoculation containing about $10^5$ cfu/ml of the bacteria.

10 µl of the bacterial suspension for inoculation (about $10^3$ cfu) was dropped by dispenser onto an MIC plate for inoculation and cultured for 7 days under the same condition as that of preculture. Thereafter, it was judged whether there had been bacteria growth or not.

iii)Judgment Standard

The minimum concentration of the sample compound when there were no visible colonies or, if any, 5 or less colonies of HP was defined as MIC (µg/ml).

Here, when the MIC value was 100 µg/ml or more, in a manner similar to the above-mentioned method, both of a MIC measurement plate with a 250 mM solution of the sample compound and a MIC measurement plate for control without a sample compound were prepared and then the bacteria was inoculated thereon in a manner similar to the above-mentioned method. As the result of the comparison of these plates, when the number of the colony on the plate containing the sample compound was less than 90% with respect to that on the control plate, it was represented by "+". Contrary to this, when there was 90% or more, it was represented by "−".

AT: Single Dose Toxicity Pretest i)Method

Male Slc:ICR mice (5-week-old) were used. Each group has 3 to 5 mice and each mouse was fasted, but allowed free access to water, for 4 to 5 hours from 9 a.m. in the test day. Then, 2,000 mg/10 ml/kg of the sample compound dissolved or suspended in an aqueous solution of 0.5% sodium carboxymethyl cellulose was orally administered thereto. To a control, only the vehicle was administered. The behavior and symptom were observed at each of 15 minutes, 30 minutes, 1 hour, 2 hours, and 3 hours after the administration and then daily till one week thereafter. The body weight was measured before and after the fasting as well as at the same time everyday. The dead animals were immediately subjected to autopsy and their organs were observed by naked eyes. Also, the living animals were sacrificed with ether or carbon dioxide one week after the administration and then their organs were observed by naked eyes.

ii)Judgment Standard

The toxicity at the single dose of 2,000 mg/kg of the sample compound was expressed as being classified into 5 levels.

5: mortality rate is 0%; no toxicity is found at all both in behavior and organs.

4: Mortality rate is 0%; while no toxicity is found in organs, slight toxicity is observed in behavior or body weight increase.

3: While there is a dead animal (though not all the animals are dead), no toxicity is found in organs.

2: Regardless of whether there is a dead animal or not, toxicity is found in organs.

1: All the animals are dead.

MTT: Cell Damaging and Protecting Effect Test i)Meaning

It is confirmed that there is no toxicity in cell level. Those having a toxicity in cell level are inappropriate as an anti-ulcer drug. Also, it can be confirmed that the effects of the sample compounds in other cell level tests do not result from their toxicity.

ii)Method

A male Japanese White rabbit (2.5 to 3 kg) was anesthetized to death by Nembutal™ and, immediately thereafter, its stomach was removed. The greater curvature of the stomach was incised so as to remove the stomach contents therefrom. After the mucosal surface was washed with HBSS (Hanks' Balanced Salt Solution), the stomach in ice-cooled HBSS was transferred to a laboratory. Then, after the pyloric antrum was removed, the gastric corpus mucosa was separated by a spatula and then minced into 2 to 3 mm³ pieces in BME (Basal Medium Eagle). Thereafter, these pieces were shaken at 120 to 130 cycles/minute for 15 minutes at 37° C. in BME 60 ml containing 280 U/ml of dispase and 30 to 50 U/ml of collagenase. Here, the concentration of collagenase was appropriately changed for each lot in view of the state of cells. The pieces were washed twice with EBSS (Earle's Balanced Salt Solution) containing 1 mM of EDTA and then shaken in MEM (Minimum Essential Medium) containing 1 mM of EDTA at 37° C. for 5 minutes. Subsequently, they were shaken in the dispase and collagenase having the same concentrations as those mentioned above for 15 minutes so as to remove the supernatant and then further shaken at 37° C. for 50 to 60 minutes at 120 to 130 cycles/minute. Then, after being washed twice with HBSS, Ham F12 containing 2% of Ultrocer G™ was used to attain the concentration of 1×10⁶ cells/ml. Thus formed suspension was dispensed in each well of a 96-well plate by 200 μl. The plate was incubated in the atmosphere composed of 5% $CO_2$ and 95% air at 37° C. for three days so as to attain a confluent state and then subjected to MTT assay.

The sample compound was dissolved in DMSO so as to attain a concentration of $10^{-2}$ M and then diluted with HBSS containing 2% of Ultrocer G™ so as to attain a final concentration of $10^{-4}$ M. To each group, which 8 wells were used for, 10 μl of MTT reagent was added immediately after 100 μl of the medium in each well was exchanged for same volume of the resulting solution of the sample compound. After being incubated in an atmosphere composed of 5% $CO_2$ and 95% air at 37° C. for 4 hours, thus formed solution was centrifuged and then its supernatant was discarded. Subsequently, 100 μl of 100% ethanol was added to the residue so as to dissolve MTT formazan. Then, the absorbance (OD: 570 to 630) was measured by a microplate reader. This method utilizes a phenomenon in which MTT is changed to MTT formazan only by mitochondria of living cells so as to change color.

iii) Judgment Standard

The cell damaging or cell protecting effect of the sample compound at the final concentration of $10^{-4}$ M was expressed as cell damaging rate (%) as follows:

cell damaging rate (%)=(1-(absorbance in sample group/absorbance in control group))×100

Accordingly, the smaller value is better in the cell damaging rate.

Based on the foregoing effect tests and safety tests, example compounds of the present invention were tested.

Compound Group 1

An alkylenediamine derivative of this compound group 1 is corresponding to formula 5 mentioned above. As the alkylenediamine derivatives of this compound group 1, the following compounds of Examples 1 to 28 were tested.

Example 1:

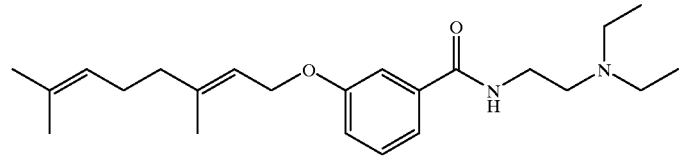

Example 2:

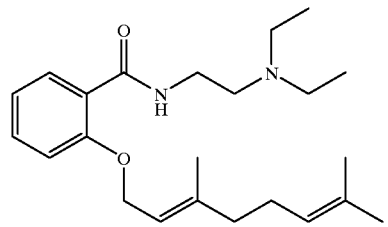

Example 3:

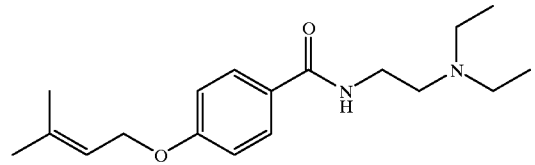

Example 4:

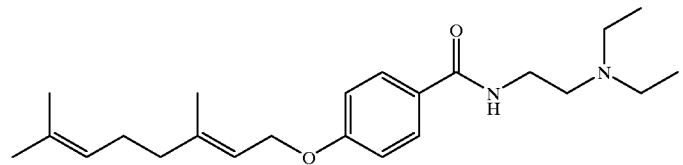

-continued
Example 5:
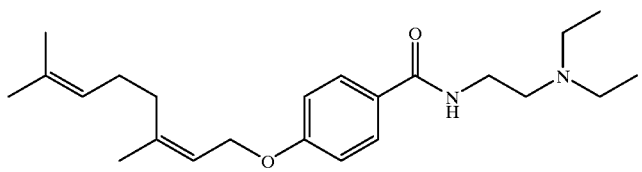
Example 6:
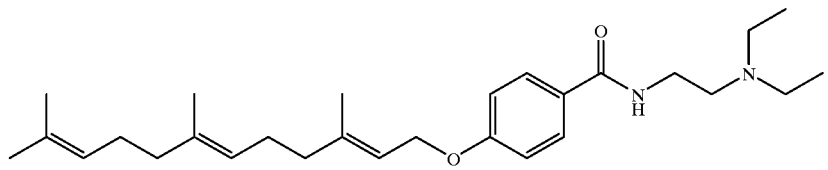
Example 7:
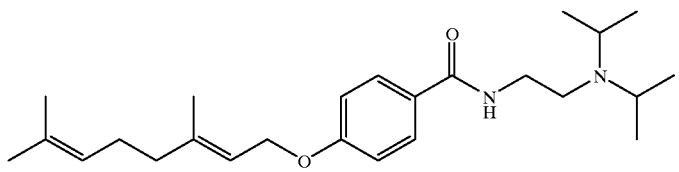
Example 8:
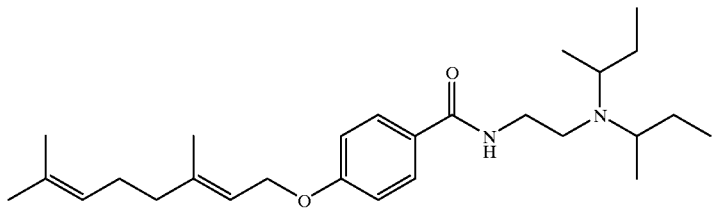
Example 9:
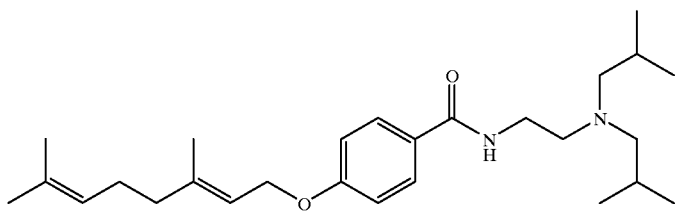
Example 10:
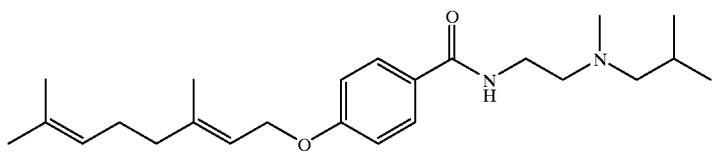
Example 11:
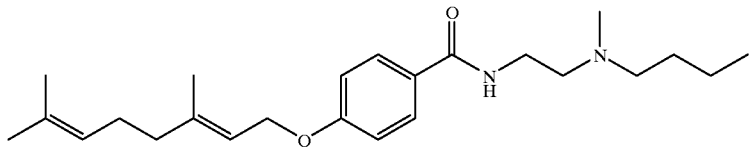
Example 12:
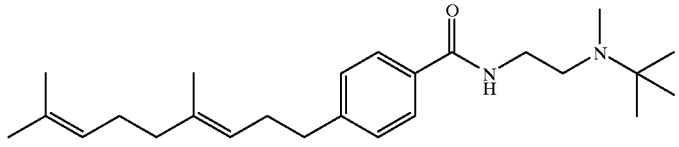

Example 13:
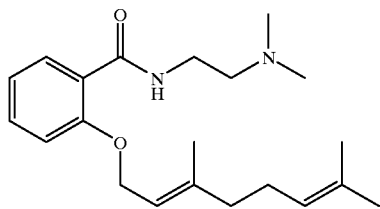
Example 14:
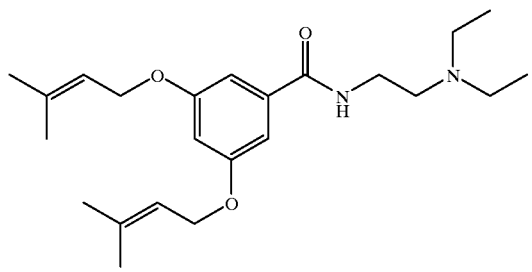
Example 15:
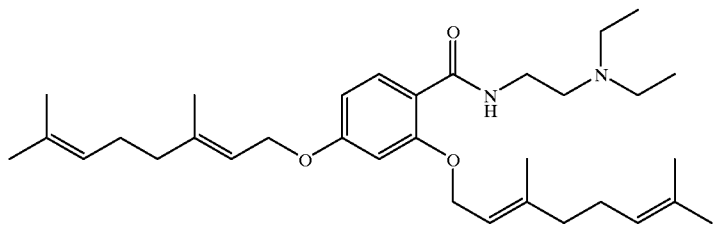
Example 16:
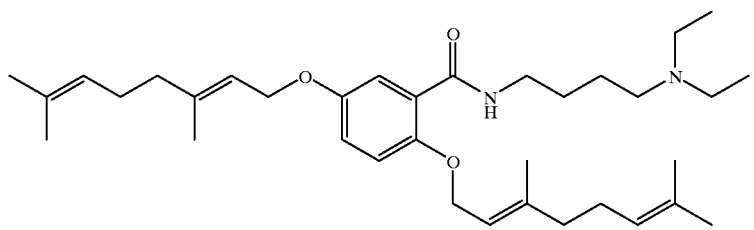
Example 17:
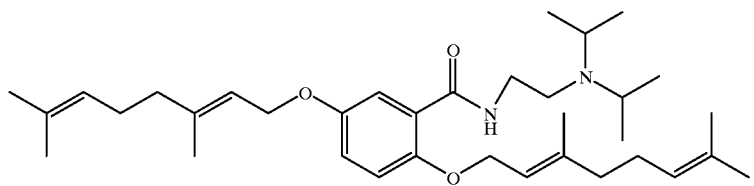
Example 18:
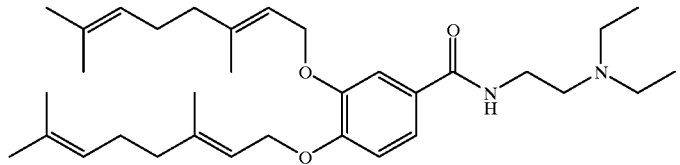

-continued
Example 19:
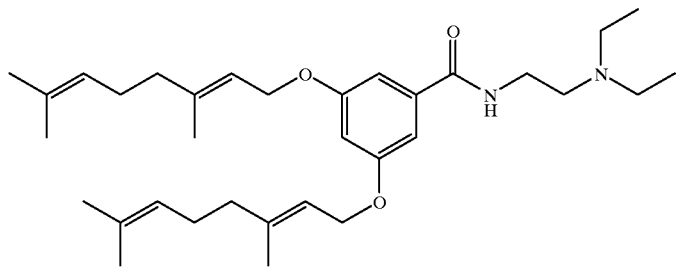
Example 20:
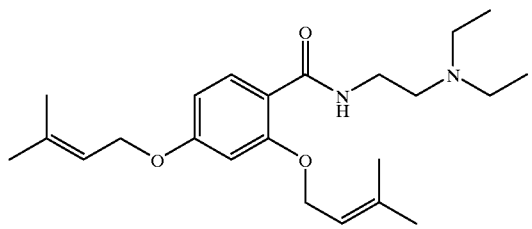
Example 21:
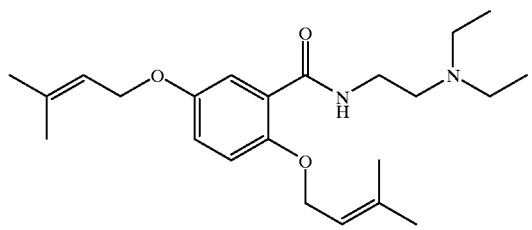
Example 22:
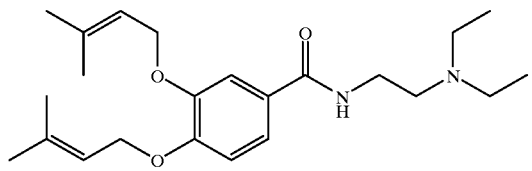
Example 23:
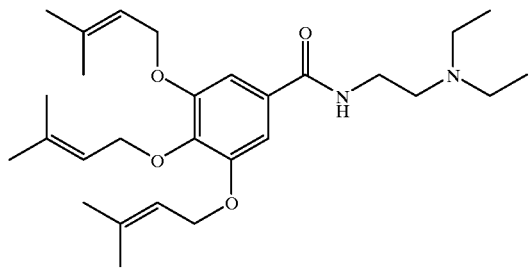
Example 24:
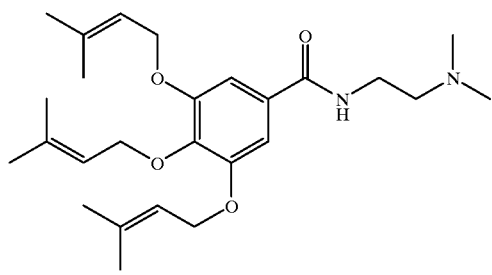

-continued

Example 25:

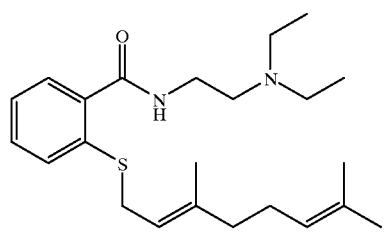

Example 26:

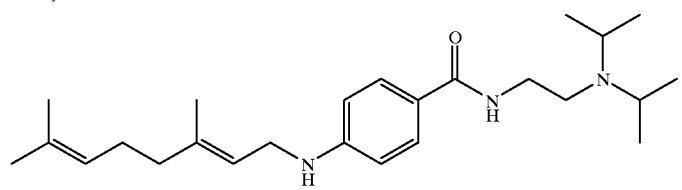

Example 27:

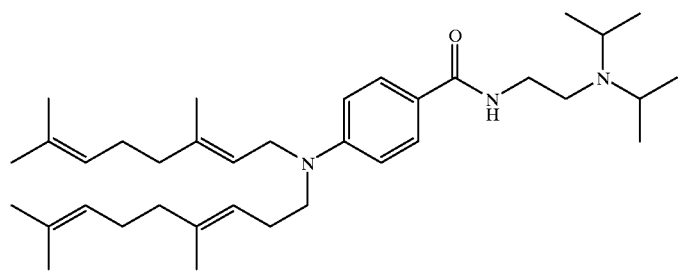

Example 28:

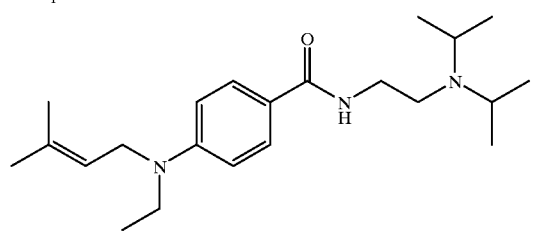

TABLE 1

| Example No. | Anti-ulcer Tests | | Anti-HP Test | Tests for Safety | |
|---|---|---|---|---|---|
| | WIS | CAP | AHP | MTT | AT |
| 1 | 72 | | | | |
| 2 | 82 | 99.9 | | 28 | |
| 3 | 88 | 70.8 | | 1 | |
| 4 | 83 | | | | |
| 5 | 90 | 109.3 | | 30 | |
| 6 | 52 | 97.9 | | | |
| 7 | 84 | 100.2 | + | | 5 |
| 8 | 58 | 99.9 | | 38 | |
| 9 | 40 | | | 15 | |
| 10 | 65 | | | | |
| 11 | 45 | 100.0 | | | |
| 12 | 34 | 99.9 | | | |
| 13 | 75 | 96.6 | | 19 | |
| 14 | 86 | 100.3 | | 43 | 5 |
| 15 | 92 | 96.5 | | 44 | |
| 16 | 82 | 100.1 | | 40 | 5 |
| 17 | 62 | 100.1 | <3.13 | 27 | 5 |
| 18 | 37 | | | | |
| 19 | 69 | | | | |
| 20 | 67 | 100.0 | | 28 | |
| 21 | 77 | 100.0 | | 36 | |
| 22 | 81 | 99.8 | | 16 | |
| 23 | 81 | | | | |
| 24 | 70 | | | | |
| 25 | 82 | 96.1 | | 19 | |
| 26 | 49 | 100.5 | | | |
| 27 | 45 | 38.5 | | 39 | |
| 28 | 87 | 27.3 | + | 16 | |

As clearly from Table 1, a compound of this compound group 1 has an excellent anti-ulcer effect and acid secretion inhibition effect, and there is a compound having a high antibacterial activity against *Helicobacter pyroli* together with. Also, it can be understood that they have high safety.

Here, in this compound group 1, though X is preferably —O—, even when X is —S— or —N($R_5$)— such as Examples 25 to 28, the effect has been maintained. While each of $R_1$ and $R_2$ can be a lower alkyl group, they are preferably ethyl or isopropyl groups from the viewpoint of the result of the anti-ulcer test.

Compound Group 2
An alkylenediamine derivative of this compound group 2 is corresponding to formula 6 mentioned above. As the alkylenediamine derivatives of this compound group 2, the following compounds of Examples 29 to 43 were tested.
Example 29:
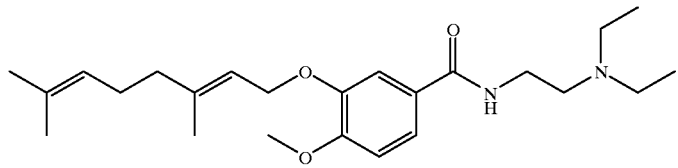
Example 30:
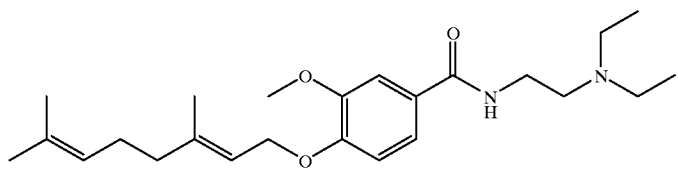
Example 31:
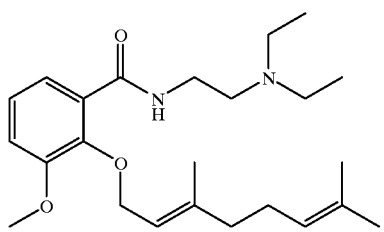
Example 32:
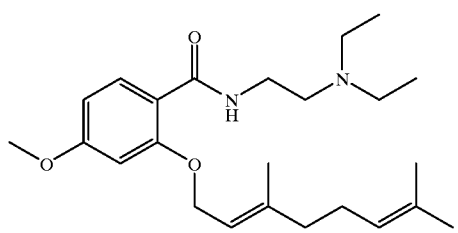
Example 33:
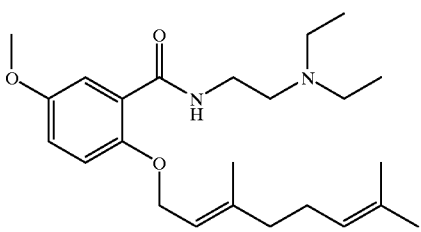
Example 34:
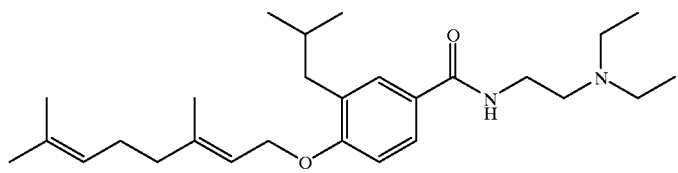

-continued
Example 35:
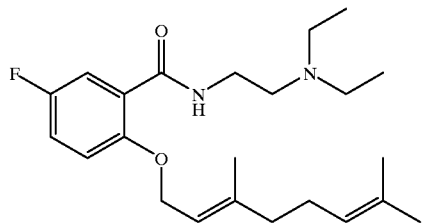
Example 36:
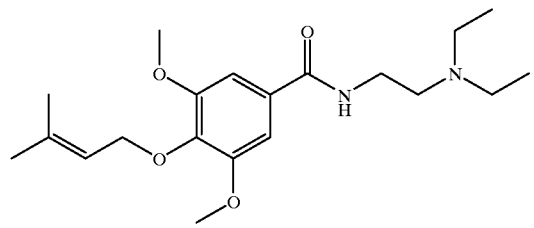
Example 37:
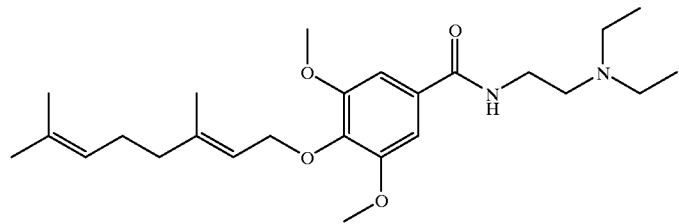
Example 38:
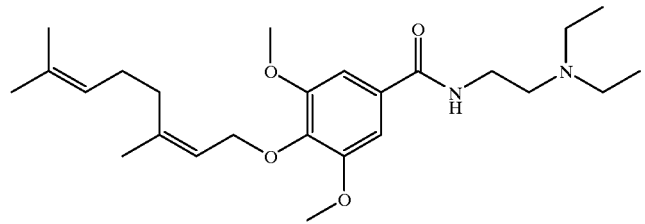
Example 39:
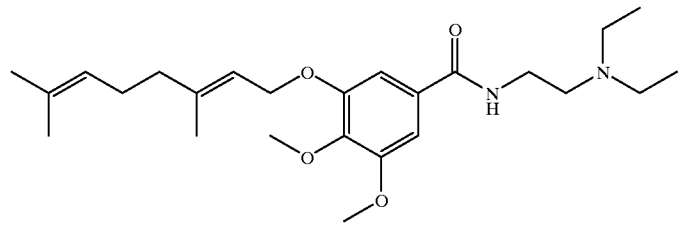
Example 40:
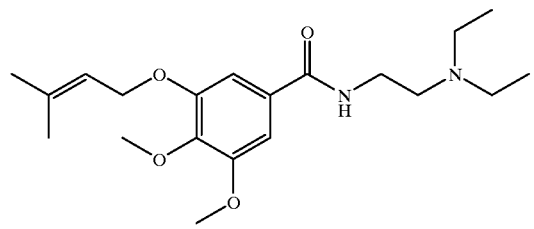

Example 41:

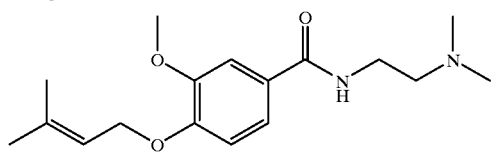

Example 42:

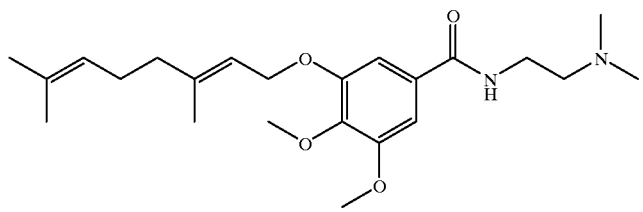

Example 43:

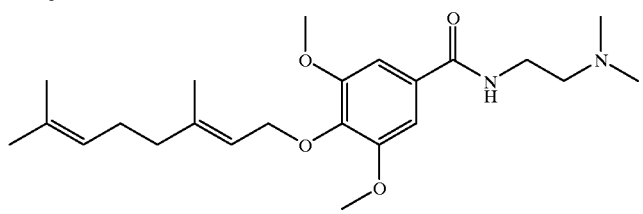

TABLE 2

| Example No. | Anti-ulcer Tests | | Tests for Safety | |
|---|---|---|---|---|
| | WIS | CAP | MTT | AT |
| 29 | 81 | 100.2 | 49 | |
| 30 | 84 | 100.1 | | 5 |
| 31 | 73 | 100.3 | 17 | |
| 32 | 73 | 100.2 | 28 | |
| 33 | 67 | 100.0 | 26 | |
| 34 | 48 | 100.3 | | |
| 35 | 81 | 105.4 | 25 | |
| 36 | 88 | | | |
| 37 | 69 | 99.3 | 39 | 4 |
| 38 | 86 | 99.8 | 30 | 5 |
| 39 | 87 | | | 4 |
| 40 | 79 | | −2 | |
| 41 | 78 | | 13 | |
| 42 | 81 | 98.6 | 17 | 3 |
| 43 | 88 | | 1 | |

As clearly from Table 2, even when a lower alkyl group, a lower alkoxy group or halogen atom is introduced into the alkylenediamine derivative of compound group 1, a high anti-ulcer effect and acid secretion inhibition effect can be exhibited. Also, it can be understood that they have high safety.

Compound Group 3

An alkylenediamine derivative of this compound group 3 is corresponding to formula 7 mentioned above. As the alkylenediamine derivatives of this compound group 3, the following compounds of Examples 44 to 55 were tested.

Example 44:

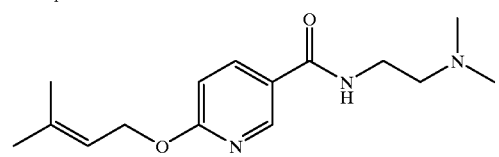

-continued
Example 45:
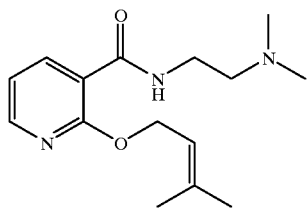
Example 46:
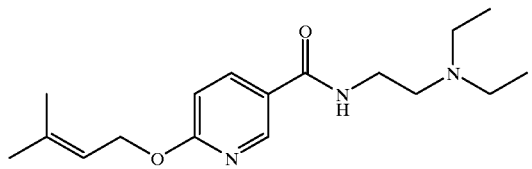
Example 47:
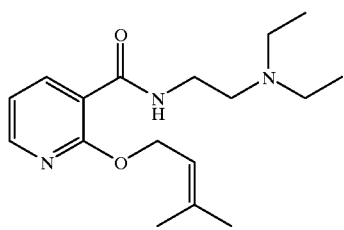
Example 48:
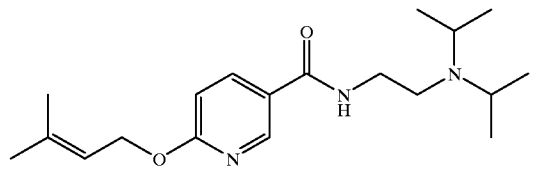
Example 49:
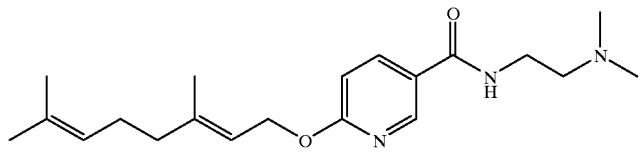
Example 50:
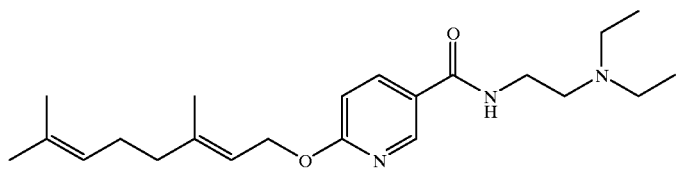
Example 51:
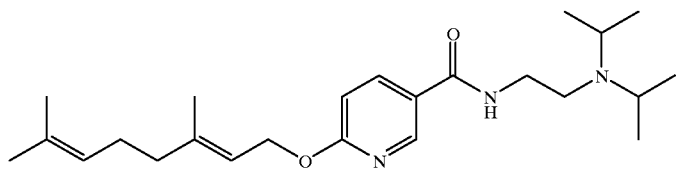

Example 52:

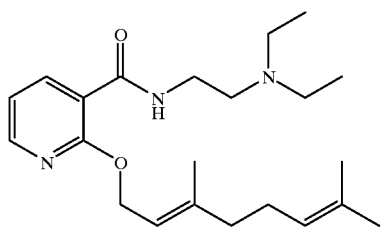

Example 53:

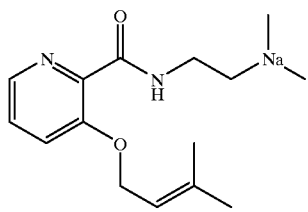

Example 54:

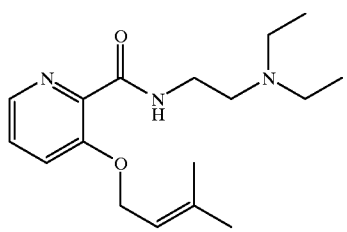

Example 55:

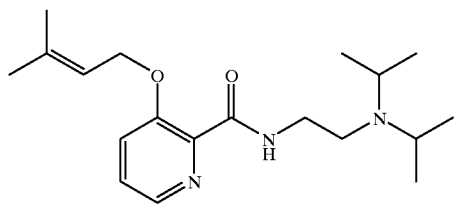

As clearly from Table 3, an alkylenediamine derivatives of this compound group 3 has an anti-ulcer effect and acid secretion inhibition effect. Also, it has been shown that they have high safety. While each of $R_1$ and $R_2$ can be a lower alkyl group, they are preferably ethyl or isopropyl groups from the viewpoint of the result of the anti-ulcer test.

TABLE 3

| Example | Anti- ulcer Tests | | Tests for Safety | |
|---|---|---|---|---|
| No. | WIS | CAP | MTT | AT |
| 44 | 30 | | | |
| 45 | 41 | | | |
| 46 | 65 | | −3 | 3 |
| 47 | 80 | | | |
| 48 | 75 | | −13 | 3 |
| 49 | 38 | | | |
| 50 | 42 | 95.2 | 4 | |
| 51 | 72 | 94.7 | 15 | |
| 52 | 57 | 100.8 | | |
| 53 | 67 | | 1 | |
| 54 | 78 | | −10 | |
| 55 | 97 | | 20 | |

Compound Group 4

An alkylenediamine derivative of this compound group 4 is corresponding to formula 8 mentioned above. As the alkylenediamine derivatives of this compound group 4, the following compounds of Examples 55 and 57 were tested.

Example 56:

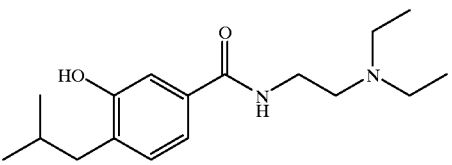

Example 57:

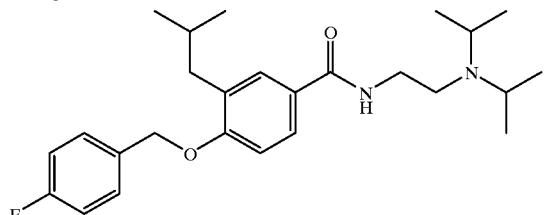

TABLE 4

| Example No. | Anti-ulcer Tests | | Tests for Safety |
|---|---|---|---|
| | WIS | CAP | MTT |
| 56 | 69 | 53.4 | 11 |
| 57 | 45 | 100.0 | 43 |

As clearly from Table 4, an alkylenediamine derivative of this compound group 4 has an anti-ulcer effect and acid secretion inhibition effect. Also, it has been shown that they have high safety.

Compound Group 5

An alkylenediamine derivative of this compound group 5 is corresponding to formula 9 mentioned above. As the alkylenediamine derivatives of this compound group 5, the following compounds of Examples 58 to 70 were tested.

Example 58:

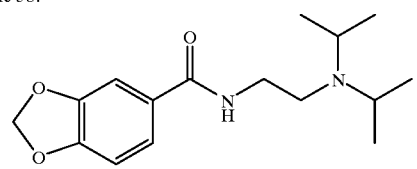

Example 59:

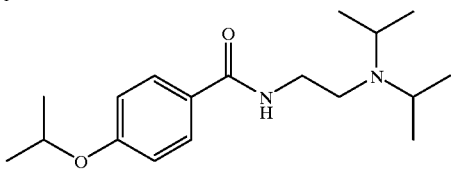

Example 60:

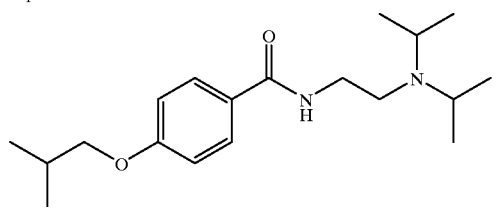

Example 61:

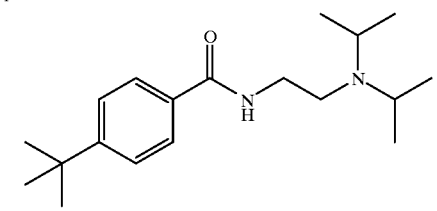

Example 62:

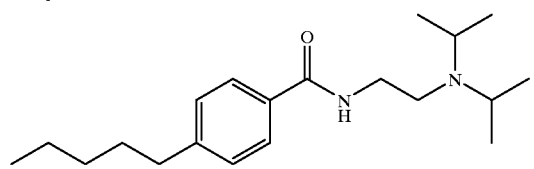

Example 63:

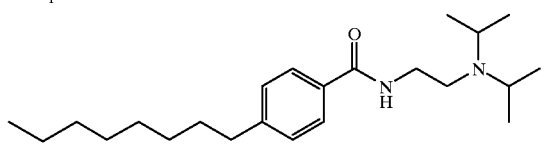

Example 64:

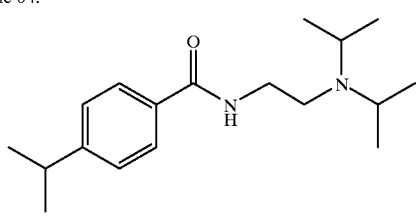

Example 65:

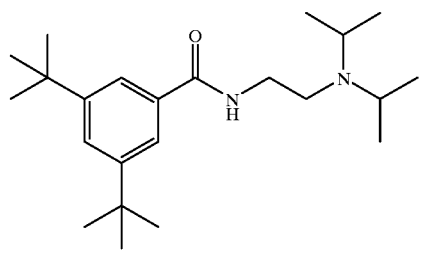

Example 66:

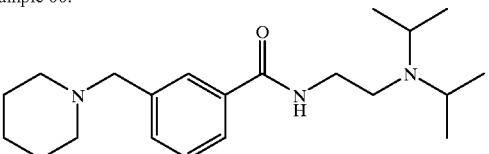

Example 67:

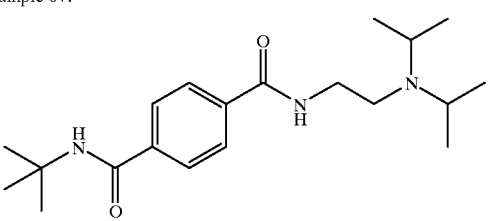

Example 68:

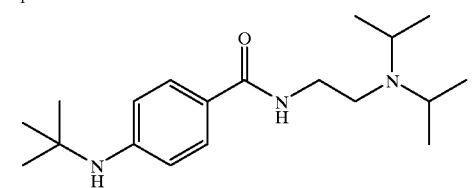

Example 69:

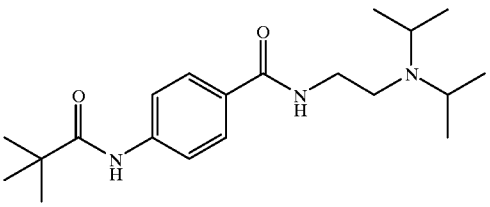

Example 70:

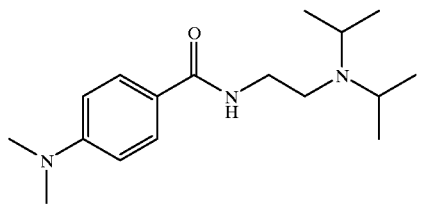

As clearly from Table 5, a compound of this compound group 5 has an anti-ulcer effect and an acid secretion inhibition effect, and there is a compound having a high antibacterial activity against *Helicobacter pyroli* together with. Also, it can be understood that they have high safety.

Here, in this compound group 5, $R_8$ has a high degree of freedom, whereby it can be selected from the group of a lower alkyl, a lower alkoxy, a piperidinoalkyl, a substituted carbamoyl, or a substituted amino group.

TABLE 5

| Example No. | Anti- ulcer Tests | | Anti- HP Test | Tests for Safety |
|---|---|---|---|---|
| | WIS | CAP | AHP | MTT |
| 58 | 96 | | | 29 |
| 59 | 89 | 47.5 | | 39 |
| 60 | 98 | 97.3 | | |
| 61 | 94 | 97.3 | 6.25 ~ 12.5 | |
| 62 | 72 | 100.9 | | 40 |
| 63 | 49 | 100.6 | | |
| 64 | 82 | 72.7 | 6.25 ~ 12.5 | 39 |
| 65 | 86 | | | 5 |
| 66 | 53 | 38.3 | | 12 |
| 67 | 77 | | | −35 |
| 68 | 79 | | | −58 |
| 69 | 95 | 31.5 | | 35 |
| 70 | 66 | 101.1 | | |

In the following, the manufacturing method of Examples of the present invention will be explained.

At first, the synthetic examples of the material compounds used for synthesizing Examples of the present invention will be shown as Reference Examples 1 to 26.

Reference Example 1

Synthesis of 4-geranyloxybenzoic acid

To a solution of methyl 4-hydroxybenzoate (7.61 g) in acetone(80 ml) were added geranyl bromide (10.9 g) and potassium carbonate (13.8 g), and then the mixture was refluxed with heating for 6 hours. After the reaction, water (150 ml) was added to the reaction mixture, and the mixture was extracted with chloroform. The organic layer was dried over sodium sulfate anhydride and then concentrated under a vacuum. The residue was purified by silica gel column chromatography (hexane:ethyl acetate=9.1), thereby yielding 13.00 g of methyl 4-geranyloxy benzoate.

To a solution of methyl 4-geranyloxybenzoate(13.00 g) in methanol(50 ml) was added aqueous solution(10 ml) of potassium hydroxide (3.90 g). After being stirred overnight at room temperature, the mixture was refluxed with heating for 1 hour. After being acidified with concentrated hydrochloric acid, the reaction mixture was extracted with chloroform. The organic layer was dried over sodium sulfate anhydride and then the solvent was evaporated out under a vacuum. The resulting solid was recrystallized from hexane/ethyl acetate mixed solution, thereby yielding 9.77 g(71%) of the aimed compound.

Reference Example 2

Synthesis of 4-prenyloxybenzoic acid

In a manner identical to Reference Example 1, from methyl 4-hydroxy benzoate (7.61 g) and prenylbromide (7.45 g), 5.86 g (57%) of 4-prenyloxybenzoic acid was obtained.

Reference Example 3

Synthesis of 3-geranyloxybenzoic acid

In a manner identical to Reference Example 1, from methyl 3-hydroxy benzoate(7.61 g) and geranylbromide (10.86 g), 8.45 g(62%) of 3-geranyloxybenzoic acid was obtained.

Reference Example 4

Synthesis of 2-geranyloxybenzoic acid

In a manner identical to Reference Example 1, from methyl-2-hydroxy benzoate(7.61 g) and geranylbromide (10.86 g), 10.23 g(75%) of 2-geranyloxybenzoic acid was obtained.

Reference Example 5

Synthesis of 4-farnesyloxybenzoic acid

In a manner identical to Reference Example 1, from methyl 4-hydroxy benzoate(5.33 g) and farnesylbromide (10.00 g), 7.58 g(63%) of 4-farnesyloxybenzoic acid was obtained.

Reference Example 6

Synthesis of 2-geranylthiobenzoic acid

In a manner identical to Reference Example 1, from methyl 2-mercapto benzoate(8.36 g) and geranylbromide (10.86 g), 10.97 g(76%) of 2-geranylthiobenzoic acid was obtained.

Reference Example 7

Synthesis of 2-geranyloxy-5-methoxybenzoic acid

To a solution of 2-hydroxy-5-methoxybenzoic acid (8.40 g) in ethanol (100 ml) was added sulfuric acid (5 ml) and then the mixture was refluxed with heating for 3 hours. After the reaction, the reaction mixture was concentrated and then water (100 ml) and sodium hydrogencarbonate were added thereto. The mixture was extracted with chloroform and the extract was purified by silica gel column chromatography (hexane:ethyl acetate), thereby yielding ethyl 2-hydroxy-5-methoxybenzoate.

In a manner identical to Reference Example 1, from the resulting compound (9.10 g) and geranylbromide(10.86 g), 7.34 g(48%) of 2-geranyloxy-5-methoxybenzoic acid was obtained.

Reference Example 8

Synthesis of 3,4-diprenyloxybenzoic acid

In a manner identical to Reference Example 1, from ethyl 3,4-dihydroxy benzoate(9.10 g) and prenylbromide(14.90 g), 11.61 g(67%) of 3,4-diprenylbenzoic acid was obtained.

Reference Example 9

Synthesis of 3,4-digeranyloxybenzoic acid

In a manner identical to Reference Example 1, from ethyl 3,4-dihydroxy benzoate(9.10 g) and geranylbromide(21.70 g), 13.1 g(62%) of 3,4-digeranyloxybenzoic acid was obtained.

Reference Example 10

Synthesis of 2,4-digeranyloxybenzoic acid

In a manner identical to Reference Example 7, from 2,4-dihydroxybenzoic acid(9.10 g) and geranylbromide (21.70 g), 8.34 g(52%) of 2,4-digeranyloxybenzoic acid was obtained.

Reference Example 11

Synthesis of 3,4-dimethoxy-5-geranyloxybenzoic acid

In a manner identical to Reference Example 1, from methyl 3,4-dimethoxy-5-hydroxybenzoate(7.00 g) and geranylbromide(10.30 g), 5.62 g(51%) of 3,4-dimethoxy-5-geranyloxybenzoic acid was obtained.

Reference Example 12

Synthesis of methyl 3,5-dimethoxy-4-hydroxybenzoate

In a manner identical to Reference Example 7, from syringe acid (17.03 g) and methanol, 13.85 g(76%) of methyl 3,5-dimethoxy-4-hydroxybenzoate was obtained.

Reference Example 13

Synthesis of 3,5-dimethoxy-4-prenyloxybenzoic acid

In a manner identical to Reference Example 1, from methyl 3,5-dimethoxy-4-hydroxybenzoate(7.89 g) and prenylchloride(5.73 g), 5.40 g(55%) of 3,5-dimethoxy-4-prenyloxybenzoic acid was obtained.

Reference Example 14

Synthesis of 3,5-dimethoxy-4-geranyloxybenzoic acid

In a manner identical to Reference Example 1, from methyl 3,5-dimethoxy-4-hydroxybenzoate(5.44 g) and geranylbromide(8.04 g), 5.71 g (67%) of 3,5-dimethoxy-4-geranyloxybenzoic acid was obtained.

Reference Example 15

Synthesis of 4-neryloxybenzoic acid

To a solution of nerol(7.71 g) in dichloromethane(200 ml) were added N-chlorosuccinimide(10.01 g) and dimethylsulfide(6.56 ml) and then the mixture was stirred while being cooled with ice for 4 hours. After the reaction, the reaction mixture was washed with saturated brine and water successively, dried over sodium sulfate anhydride, and concentrated.

In a manner identical to Reference Example 1, from nergylchloride obtained and methyl 4-hydroxybenzoate (7.61 g), 7.47 g (54%) of 4-neryloxybenzoic acid was obtained.

Reference Example 16

Synthesis of 3,4,5-triprenyloxybenzoic acid

In a manner identical to Reference Example 1, from ethyl 3,4,5-trihydroxy benzoate(4.95 g) and prenylbromide(14.90 g), 5.43 g(58%) of 3,4,5-triprenyloxybenzoic acid was obtained.

Reference Example 17

Synthesis of 2-geranyloxy-4-methoxybenzoic acid

In a manner identical to Reference Example 1, from methyl 2-hydroxy-4-methoxybenzoate(9.1 g) and geranylbromide(10.86 g), 7.73 g(51%) of 2-geranyloxy-4-methoxybenzoic acid was obtained.

Reference Example 18

Synthesis of 4-geranyloxy-3-methoxybenzoic acid

In a manner identical to Reference Example 1, from methyl 4-hydroxy-3-methoxybenzoate(9.1 g) and geranylbromide(10.86 g), 7.59 g(63%) of 4-geranyloxy-3-methoxybenzoic acid was obtained.

Reference Example 19

Synthesis of 2-geranyloxy-3-methoxybenzoic acid

In a manner identical to Reference Example 7, from 2-hydroxy-3-methoxybenzoic acid(16.80 g) and geranylbromide(10.86 g), 11.54 g(64%) of 2-geranyloxy-3-methoxybenzoic acid was obtained.

Reference Example 20

Synthesis of 3-geranyloxy-4-methoxybenzoic acid

In a manner identical to Reference Example 1, from methyl 3-hydroxy-4-methoxybenzoate(8.40 g) and geranylbromide(10.36 g), 3.60 g(24%) of 3-geranyloxy-4-methoxybenzoic acid was obtained.

Reference Example 21

Synthesis of 3,5-diprenyloxybenzoic acid

In a manner identical to Reference Example 1, from methyl 3,5-dihydroxy benzoate(8.40 g) and prenylbromide (14.90 g), 10.06 g(69%) of 3,5-diprenyloxybenzoic acid was obtained.

Reference Example 22

Synthesis of 2,4-diprenyloxybenzoic acid

In a manner identical to Reference Example 1, from methyl 2,4-dihydroxy benzoate(8.40 g) and prenylbromide (14.90 g), 8.86 g(61%) of 2,4-diprenyloxybenzoic acid was obtained.

Reference Example 23

Synthesis of 2,5-diprenyloxybenzoic acid

In a manner identical to Reference Example 7, from methyl 2,5-dihydroxy benzoic acid (23.10 g) and prenylbromide (14.90 g), 9.74 g(84%) of 2,5-diprenyloxy benzoic acid was obtained.

Reference Example 24

Synthesis of 3,5-digeranyloxybenzoic acid

In a manner identical to Reference Example 1, from methyl 3,5-dihydroxy benzoate (8.40 g) and geranylbromide (21.74 g), 10.09 g(47%) of 3,5-digeranyloxy benzoic acid was obtained.

Reference Example 25

Synthesis of 2,5-digeranyloxybenzoic acid

In a manner identical to Reference Example 1, from methyl 2,5-dihydroxy benzoate(7.12 g) and geranylbromide (21.72 g), 2.17 g(10%) of 2,5-digeranyloxybenzoic acid was obtained.

Reference Example 26

Synthesis of 3-fluoro-6-geranyloxybenzoic acid

In a manner identical to Reference Example 7, from 3-fluoro-6-hydroxybenzoic acid(10.00 g) and geranylbromide(10.86 g), 11.57 g(79%) of 3-fluoro-6-geranyloxybenzoic acid was obtained.

EXAMPLE 1

3-geranyloxybenzoic acid(1.37 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.74 g(94%) of the aimed compound.

$^1$H-NMR (CDCl$_3$)δ : 7.42–7.25 (3H, m), 7.03(2H, dt, J=2.4 Hz, 7.3 Hz), 6.99(1H, bs), 5.49(1H, t, J=6.4 Hz), 5.17–5.04(1H, m),4.58(2H, d, J=6.4 Hz), 3.48(2H, q, J=5.4 Hz), 2.66(2H, t, J=5.9 Hz), 2.58(4H, q. J=7.3 Hz), 2.19–2.03 (4H, m), 1.74(3H, s), 1.68(3H, s), 1.60(3H, s), 1.05(6H, t, J=7.3 Hz).

EXAMPLE 2

2-geranyloxybenzoic acid(1.37 g) was dissolved in chloroform(40 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 15 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.1 g(59%) of the aimed compound.

$^1$H-NMR (CDCl$_3$)δ : 8.37(1H, bs), 8.22(1H, dd, J=2.0 Hz, 7.8 Hz), 7.39(1H, dt, J=2.0 Hz, 8.3 Hz), 7.03(1H, t, J=7.8 Hz), 6.94(1H, d, J=8.3 Hz), 5.51(1H, t, J=6.4 Hz), 5.12–5.03 (1H, m), 4.71(2H, d, J=6.4 Hz), 3.54(2H, d, J=6.4 Hz), 2.64(2H, t, J=6.4Hz), 2.84(4H, q, J=7.3 Hz), 2.16–2.03(4H, m), 1.75(3H, s), 1.67(3H, s), 1.60(3H, s), 1.03(6H, t, J=7.3 Hz).

EXAMPLE 3

4-prenyloxybenzoic acid(1.44 g) was dissolved in chloroform(40 ml) and triethylamine(1.35 ml), and then diphenylphosphinic chloride(1.33 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 1.11 g(52%) of the aimed compound.

$^1$H-NMR (CDCl$_3$)δ : 7.74(2H, d, J=8.8 Hz), 7.00(1H, bs), 6.91(2H, d, J=8.8 Hz), 5.48(1H, t, J=7.9 Hz), 4.54(2H, d, J=7.9 Hz), 3.49(2H, q, J=7.0 Hz), 2.67(2H, t, J=7.0 Hz), 2.59(4H, q, J=7.0 Hz), 1.80(3H, s), 1.74(3H, s), 1.08–1.03 (6H, m).

EXAMPLE 4

4-geranyloxybenzoic acid(1.37 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 15 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.58 g(85%) of the aimed compound.

$^1$H-NMR (CDCl$_3$)δ : 7.73(2H, d, J=8.8 Hz), 6.95(1H, bs), 6.91(2H, d, J=8.8 Hz), 5.47(1H, t, J=6.8 Hz), 5.13–5.05(1H, m), 4,57(2H, d, J=6.4 Hz), 3.51(2H, q, J=5.4 Hz), 2.67(2H, t, J=5.9 Hz), 2.59(4H, q, J=7.3 Hz), 2.20–2.14(4H, m), 1.74(3H, s), 1.71(3H, s), 1.67(3H, s), 1.05(6H, t, J=7.3 Hz).

EXAMPLE 5

4-neryloxybenzoic acid(1.64 g) was dissolved in chloroform(40 ml) and triethylamine(1.63 ml), and then diphenylphosphinic chloride(1.15 ml) was added thereto while being cooled with ice. After being stirred for 15 minutes, the mixture, with N,N-diethylethylenediamine (0.84 ml) added thereto, was stirred for 1.5 hours at room temperature. The reaction mixture was washed with saturated sodium hydrogencarbonate aqueous solution and saturated brine successivel, dried over sodium sulfate anhydride, and then concentrated under a vacuum. The residue was purified by silica gel column chromatography (chloroform:methanol=15:1), thereby yielding 1.15 g(52%) of the aimed compound.

$^1$H-NMR (CDCl$_3$)δ : 7.75(2H, d, J=8.3 Hz), 7.16(1H, bs), 6.86(2H, d, J=6.6 Hz), 5.49(1H, t, J=6.9 Hz), 5.13–5.11(1H, m), 4.58(2H, d, J=5.4 Hz), 3.52(2H, q, J=5.4 Hz), 2.72(2H, t, J=5.9 Hz), 2.64(4H, q, J=7.7 Hz), 2.17–2.08(8H, m), 1.80(3H, s), 1.68(3H, s), 1.60(3H, s), 1.07(6H, t, J=7.1 Hz).

EXAMPLE 6

4-farnesyloxybenzoic acid(1.71 g) was dissolved in chloroform(40 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.99 g(90%) of the aimed compound.

$^1$H-NMR (CDCl$_3$)δ : 7.73(2H, d, J=8.8 Hz), 6.94(2H, d, J=8.8 Hz), 6.66(1H, bs), 5.48(1H, t, J=5.4 Hz), 5.16–5.06 (2H, m), 4.58(2H, d, J=5.4 Hz), 3.49(2H, q, J=7.0 Hz), 2.67(2H, t, J=7.0 Hz), 2.59(4H, q, J=7.0 Hz), 2.17–1.92(8H, m), 1.75(3H, s), 1.68(3H, s), 1.60(6H, s), 1.05(6H, t, J=7.1 Hz).

EXAMPLE 7

4-geranyloxybenzoic acid(1.64 g) was dissolved in chloroform(50 ml) and triethylamine(1.67 ml), and then diphenylphosphinic chloride(1.15 ml) was added thereto while being cooled with ice. After being stirred for 15 minutes, the mixture, with N,N-diisopropylethylenediamine (1.04 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=30:1), thereby yielding 1.20 g(50%) of the aimed compound.

$^1$H-NMR (CDCl$_3$)δ : 7.35(2H, d, J=8.8 Hz), 6.90(2H, d, J=8.8 Hz), 5.48(1H, t, J=5.4 Hz), 5.17–5.02(1H, m), 4.56 (2H, d, J=6.4 Hz), 3.06–2.65(2H, m), 2.63–2.40(6H, m), 2.21–1.99(4H, m), 1.74(3H, s), 1.68(3H, s), 1.60(3H, s), 1.97–1.34(11H, m).

EXAMPLE 8

4-geranyloxybenzoic acid(1.19 g) was dissolved in chloroform(50 ml) and triethylamine(1.20 ml), and then diphenylphosphinic chloride(0.83 ml) was added thereto while being cooled with ice. After being stirred for 15 minutes, the mixture, with N,N-di-sec-butylethyleneidamine (0.76 g) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 0.75 g(40%) of the aimed compound.

$^1$H-NMR (CDCl$_3$)δ : 7.72(2H, d, J=8.3 Hz), 6.92(2H, d, J=8.3 Hz), 6.91–6.62(1H, m), 5.48(1H, t, J=6.4 Hz), 5.09 (1H, t, J=6.0 H), 4.57(2H, d, J=6.4 Hz), 3.72–3.13(3.72(2H, m), 2.93–2.43(4H, m), 2.27–1.95(4H, m), 1.74(3H, s), 1.68 (3H, s), 1.66–1.07(4H, m), 1.60(6H, s), 1.03(3H, d, J=6.4 Hz), 0.99(3H, d, J=6.4 Hz), 0.90(6H, t, J=7.3 Hz).

EXAMPLE 9

4-geranyloxybenzoic acid(2.74 g) was dissolved in chloroform(50 ml) and triethylamine(2.02 g), and then diphenylphosphinic chloride(2.37 g) was added thereto while being cooled with ice. After being stirred for 15 minutes, the mixture, with N,N-diisobutylethylenediamine (1.65 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=40:1), thereby yielding 0.68 g(16%) of the aimed compound.

$^1$H-NMR (CDCl$_3$)δ : 7.72(2H, d, J=8.8 Hz), 6.93(2H, d, J=8.8 Hz), 5.48(1H, t, J=6.8 Hz), 5.12–5.04(1H, m), 4.57 (2H, d, J=6.8 Hz), 3.61–3.42(2H, m), 2.56(2H, t, J=5.9 Hz), 2.18–2.03(8H, m), 1.74(3H, s), 1.67(3H, s), 1.60(3H, s), 0.90(12H, d, J=6.8 Hz).

EXAMPLE 10

4-geranyloxybenzoic acid(3.29 g) was dissolved in chloroform(50 ml) and triethylamine(1.67 ml), and then diphenylphosphinic chloride(2.84 g) was added thereto while being cooled with ice. After being stirred for 15 minutes, the mixture, with N-isobutyl-N-methylethylenediamine(1.56 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=40:1), thereby yielding 1.86 g(40%) of the aimed compound.

$^1$H-NMR (CDCl$_3$)δ : 7.73(2H, d, J=8.8 Hz), 6.92(2H, d, J=8.8 Hz), 6.98–6.82(1H, m), 5.48(1H, t, J=6.3 Hz), 5.09 (1H, t, J=6.3 Hz), 4.57(2H, d, J=6.3 Hz), 3.49(2H, q, J=5.9 Hz), 2.55(2H, t, J=5.9 Hz), 2.22(3H, s), 2.13(2H, d, J=7.3 Hz), 2.21–2.01(8H, m), 1.87–1.07(1H, m), 1,74(3H, s), 1.67(3H, s), 1.60(3H, s), 0.91(6H, d, J=6.4 Hz).

EXAMPLE 11

4-geranyloxybenzoic acid(1.92 g) was dissolved in chloroform(50 ml) and triethylamine(1.95 ml), and then diphenylphosphinic chloride(1.34 ml) was added thereto while being cooled with ice. After being stirred for 15 minutes, the mixture, with N-butyl-N-methylethylenediamine(1.00 g) added thereto, was stirred for 1 hour at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=30:1), thereby yielding 1.09 g(40%) of the aimed compound.

$^1$H-NMR (CDCl$_3$)δ : 7.76(2H, d, J=8.8 Hz), 7.33–7.18 (5H, m), 6.96(2H, d, J=8.8 Hz), 6.69(1H, bs), 5.51–5.42(1H, m), 5.13–5.02(1H, m), 4.57(2H, d, J=6.8 Hz), 3.57(2H, s), 3.48(2H, q, J=5.9 Hz), 2.59(2H, t, J=7.3 Hz), 2.19(3H, s), 2.17–2.02(4H, m), 1.74(3H, s), 1.68(3H, s), 1.61(3H, s).

EXAMPLE 12

4-geranyloxybenzoic acid(1.92 g) was dissolved in chloroform(50 ml) and triethylamine(1.95 ml), and then diphenylphosphinic chloride(1.34 ml) was added thereto while being cooled with ice. After being stirred for 15 minutes, the mixture, with N-tert-butyl-N-methylethylenediamine(1.56 g) added thereto, was stirred for 2 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 0.87 g(32%) of the aimed compound.

$^1$H-NMR (CDCl$_3$)δ : 7.82(2H, d, J=8.3 Hz), 7.25–7.39 (1H, m), 6.89(2H, d, J=8.3 Hz), 5.48(1H, t, J=6.3 Hz), 5.13–5.02(1H, m), 4.56(2H, d, J=6.8 Hz), 3.67–3.43(2H, m), 2.89–2.60(2H, m), 2.34(3H, s), 2.00–2.18(4H, m), 1.74(3H, s), 1.68(3H, s), 1.60(3H, s), 1.16(9H, s).

EXAMPLE 13

In a manner identical to Example 1, 2-geranyloxybenzoic acid was subjected to a condensation reaction with N,N-dimethylethylenediamine, thereby yielding the aimed compound.

EXAMPLE 14

3,5-diprenyloxybenzoic acid(1.45 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.03 g(53%) of the aimed compound.

$^1$H-NMR (CDCl$_3$)δ : 6.92(2H, d, J=2.0 Hz), 6.61(1H, t, J=2.2 Hz), 5.49(2H, t, J=6.3 Hz), 4.51(4H, d, J=6.3 Hz), 3.47(2H, q, J=5.9 Hz), 2.64(2H, t, J=6.2 Hz), 2.56(4H, q, J=7.1 Hz), 1.80(6H, s), 1.74(6H, s), 1.03(6H, t, J=7.1 Hz).

EXAMPLE 15

2,4-digeranyloxybenzoic acid(2.13 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (choroform:methanol=15.1), thereby yielding 2.28 g(87%) of the aimed compound.

$^1$H-NMR (CDCl$_3$)δ : 8.24–8.12(2H, m), 6.59(1H, d, J=8.8 Hz), 6.50(1H, s), 5.54–5.43(2H, m), 5.09–5.07(2H, m), 4.64(2H, d, J=6.4 Hz), 4.54(2H, d, J=6.8 Hz), 3.53(2H, q, J=6.4 Hz), 2.65(2H, t, J=6.4 Hz), 2.58(4H, q, J=7.3 Hz), 2.14–2.02(8H, m), 1.74(6H, s), 1.68–1.67(6H, m), 1.04(6H, t, J=7.3 Hz).

EXAMPLE 16

2,5-digeranyloxybenzoic acid(2.13 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15.1), thereby yielding 1.43 g(54%) of the aimed compound.

$^1$H-NMR (CDCl$_3$)δ : 8.47(1H, bs), 7.79(1H, d, J=2.9 Hz), 6.97(1H, dd, J=2.9 Hz, 8.8 Hz), 6.88(1H, d, J=8.8 Hz), 5.53–5.42(2H, m), 5.11–5.02(2H, m), 4.64(2H, d, J=6.3 Hz), 4.54(2H, d, J=6.4 Hz), 3.54(2H, q, J=6.3 Hz), 2.64(2H, t, J=6.3 Hz), 2.58(4H, q, J=7.3 Hz), 2.17–2.02(8H, m), 1.72 (6H, s), 1.67(6H, s), 1.60(6H, s), 1.03(6H, t, J=7.3 Hz).

EXAMPLE 17

2,5-digeranyloxybenzoic acid(1.44 g) was dissolved in tetrahydrofuran (30 ml), and then N,N'-carbonyldiimidazole (0.59 g) was added thereto while being cooled with ice. After being stirred for 1.5 hours, the mixture, with N,N-diisopropylethylenediamine(0.58 ml) added thereto, was stirred for one night at room temperature. The reaction mixture was concentrated under a vacuum, and the residue, with saturated sodium hydrogencarbonate aqueous solution (60 ml) added thereto, was extracted with ethyl acetate. The extract was washed with water and saturated brine successively, dried over sodium sulfate anhydride, and then concentrated under a vacuum. The residue was purified by silica gel column chromatography (chloroform:methanol=20:1), thereby yielding 0.71 g(39%) of the aimed compound.

EXAMPLE 18

3,4-digeranyloxybenzoic acid(2.13 g) was dissolved in chloroform(50 ml) and triethylamine(1.4 ml), and then diphenylphosphinic chloride(1.0 ml) was added thereto while being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 2.39 g(31%) of the aimed compound.

$^1$H-NMR (CDCl$_3$)δ : 7.43(1H, d, J=2.0 Hz), 7.28–7.23 (1H, m), 6.87(1H, d, J=8.3 Hz), 5.56–5.45(2H, m), 5.12–5.03(2H, m), 4.66(4H, d, J=6.4 Hz), 3.53(2H, q, J=6.4 Hz), 2.64(2H, q, J=6.4 Hz), 2.56(4H, q, J=7.3 Hz), 2.15–2.00(8H, m), 1.74(3H, s), 1.72(3H, s), 1.66(6H, s), 1.60(6H, s), 1.06(6H, t, J=7.3 Hz).

EXAMPLE 19

3,5-digeranyloxybenzoic acid(2.13 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 2.28 g(87%) of the aimed compound.

$^1$H-NMR (CDCl$_3$)δ : 6.92(2H, d, J=2.0 Hz), 6.61(1H, s), 5.49(2H, t, J=6.4 Hz), 5.12–5.04(2H, m), 4.54(4H, d, J=6.8 Hz), 3.47(2H, q, J=5.9 Hz), 2.64(2H, t, J=5.9 Hz), 2.56(4H, q, J=6.8 Hz), 2.17–2.04(8H, m), 1.73(6H, s), 1.68( 6H, s), 1.60(6H, s), 1.04(6H, t, J=7.3 Hz).

EXAMPLE 20

2,4-diprenyloxybenzoic acid(1.45 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethyethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.84(95%) of the aimed compound.

$^1$H-NMR (CDCl$_3$)δ : 8.24–8.12(2H, m), 6.59(1H, d, J=8.8 Hz), 6.50(1H, s), 5.54–5.43(2H, m), 4.64(2H, d, J=6.4 Hz), 4.54(2H, d, J=6.8 Hz), 3.53(2H, q, J=6.4 Hz), 2.65(2H, t, J=6.4 Hz), 2.58(4H, q, J=7.3 Hz), 1.80(6H, s), 1.75(6H, s), 1.04(6H, t, J=7.3 Hz).

EXAMPLE 21

2,5-diprenylbenzoic acid(1.45 g) was dissolved in chloroform(50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15.1), thereby yielding 1.44 g(74%) of the aimed compound.

$^1$H-NMR (CDCl$_3$)δ : 8.45(1H, bs), 7.77(1H, d, J=3.4 Hz), 6.98(1H, dd, J=3.4 Hz, 8.8 Hz), 6.89(1H, d, J=8.8 Hz), 5.54–4.98(2H, m), 4.63(2H, d, J=6.4 Hz), 4.51(2H, d, J=6.4 Hz), 3.51(2H, q, J=5.9 Hz), 2.70(2H, t, J=5.9 Hz), 2.62(4H, q, J=7.3 Hz), 1.79(6H, s), 1.74(6H, s), 1.07(6H, t, J=7.3 Hz).

EXAMPLE 22

3,4-diprenyloxybenzoic acid(1.45 g) was dissolved in chloroform(50 ml) and triethylamine(1.4 ml), and then diphenylphosphinic chloride(0.95 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The depositing crystals were recrystallized, thereby yielding 1.38 g(71%) of the aimed compound.

$^1$H-NMR (CDCl$_3$)δ : 7.43(1H, d, J=2.0 Hz), 6.85(1H, d, J=8.3 Hz), 5.56–5.46(2H, m), 4.62(4H, d, J=6.8 Hz), 3.48 (2H, q, J=5.4 Hz), 2.67(2H, t, J=5.4 Hz), 2.59(4H, q, J=6.8 Hz), 2.15–2.00(8H, m), 1.77(6H, s), 1.73(6H), s), 1.05(6H, t, J=7.1 Hz).

EXAMPLE 23

3,4,5-triprenyloxybenzoic acid(1.12 g) was dissolved in chloroform(35 ml) and triethylamine(0.67 g), and then diphenylphsophinic chloride(0.78 g) was added thereto while being cooled with ice. After being stirred for 30 minutes, the mixture, with N,N-diethylethylenediamine (0.38 g) added thereto, was stirred for 3 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=200:1), thereby yielding 1.15(81%) of the aimed compound.

$^{1k}$H-NMR (CDCl$_3$)δ :7.00(2H, m), 6.60(1H, m), 5.57–5.41(3H, m), 4.62–4.45 (6H, m), 3.75–3.63(4H, m), 3.56–3.45(4H, m), 2.62–2.53(2H, m), 2.52–2.40(4H, m), 1.78–1.55(18H, m).

EXAMPLE 24

3,4,5-triprenyloxybenzoic acid(1.05 g) was dissolved in chloroform(40 ml) and triethylamine(0.62 g), and then diphenylphosphinic chloride(0.73 g) was added thereto while being cooled with ice. After being stirred for 30 minutes, the mixture, with N,N-dimethylethylenediamine (0.27 g) added thereto, was stirred for 1 hour at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=200:1 to 10:1), thereby yielding 1.15 g(97%) of the aimed compound.

$^1$H-NMR (CDCl$_3$)δ : 7.01(2H, s), 6.73(1H, s), 5.59–5.45 (3H, m), 4.60(4H, d, J=6.8 Hz), 4.54(2H, d, J=6.8 Hz), 3.55–3.47(2H, m), 2.53(2H, d, J=5.9 Hz), 2.28(6H, s), 1.77(6H, s), 1.74(9H, s), 1.66(3H, s).

EXAMPLE 25

2-geranylthiobenzoic acid(2.03 g) was dissolved in chloroform(40 ml) and triethylamine(1.95 ml), and then diphenylphosphinic chloride(1.3 ml) was added thereto while being cooled with ice. After being stirred for 15 minutes, the mixture with N,N-diethylethylenediamine(1.0 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 0.96 g(35%) of the aimed compound.

$^1$H-NMR (CDCl$_2$)δ : 7.83–7.73(1H, m), 7.62(1H, d, J=7.8 Hz), 7.36–7.13(2H, m), 5.28(1H, t, J=7.8 Hz), 5.05(1H, t, J=6.4 Hz), 4.71(2H, d, J=6.4 Hz), 3.67–3.62(2H, m), 3.54 (2H, t, J=7.8 Hz), 2.89–2.75(6H, m), 2.10–1.97(4H, m), 1.66(3H, s), 1.58(6H, s, 1.14(6H, t, J=6.8 Hz).

EXAMPLE 26

4-geranylaminobenzoic acid(1.91 g) was dissolved in chloroform(38 ml) and triethylamine(1.95 ml), and then diphenylphosphinic chloride(1.33 ml) was added thereto while being cooled with ice. After being stirred for 15 minutes, the mixture, with N,N-diisopropylethylenediamine (1.22 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 2.27 g(81%) of the aimed compound.

$^1$H-NMR (CDCl$_3$)δ : 7.63(2H, d, J=8.3 Hz), 6.73–6.84 (1H, bs), 6.57(2H, d, J=8.3 Hz), 5.38–5.25(1H, m), 3.13(2H, m), 2.68(2H, t, J=5.9 Hz), 1.96–2.18(4H, m), 1.71(3H, s), 1.68(3H, s), 1.60(3H, s), 1.04(12H, t, J=6.4 Hz).

EXAMPLE 27

4-digeranylaminobenzoic acid(2.00 g) was dissolved in chloroform(40 ml) and triethylamine(1.36 ml), and then diphenylsphosphinic chloride(0.94 ml) was added thereto while being cooled with ice. After being stirred for 15 minutes, the mixture, with N,N-diisopropylethylenediamine (0.86 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 1.62 g(68%) of the aimed compound.

$^1$H-NMR (CDCl$_3$)δ : 7.64(2H, d, J=8.8 Hz), 6.80–6.70 (1H, bt), 6.64(2H, d, J=8.8 Hz), 5.18(2H, t, J=5.4 Hz), 5.10–5.02(2H, m), 3.92(4H, d, J=5.9 Hz), 3.40(2H, q, J=5.9 Hz), 3.13–2.99(2H, m), 2.68(2H, t, J=5.9 Hz), 2.16–1.94 (8H, m), 1.69(6H, s, 1.66(6H, s), 1.58(6H, s), 1.04(12H, d, J=6.8 Hz).

EXAMPLE 28

4-(N-ethyl-N-prenylamino)benzoic acid(1.74 g) was dissolved in chloroform(35 ml) and triethylamine(2.10 ml), and then diphenylphosphinic chloride (1.44 ml) was added thereto while being cooled with ice. After being stirred for 15 minutes, the mixture, with N,N-diisopropylethylenediamine (1.32 ml) added thereto, was stirred for 15 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 1.06 g(40%) of the aimed compound as a pale solid. m.p. 52.3–54.6° C.

$^1$H-NMR (CDCl$_3$)δ : 7.65(2H, d, J=8.8 Hz), 6.82–6.70 (1H, bs), 6.32(2H, d, J=9.3 Hz), 5.22–5.12(1H, m), 3.90(2H, d, J=5.9 Hz), 3.45–3.35(4H, m), 3.14–3.00(2H, m), 2.68(2H, t, J=5.9 Hz), 1.73(6H, s), 1.17(3H, t, J=7.3 Hz), 1.04(12H, d, J=6.4 Hz).

EXAMPLE 29

3-geranyloxy-4-methoxybenzoic acid(1.52 g) was dissolved in chloroform (50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.67 g(83%) of the aimed compound.

$^1$H-NMR (CDCl$_3$)δ : 7.45(1H, d, J=2.0 Hz), 6.87(1H, d, J=8.0 Hz), 5.53(1H, t, J=5.4 Hz), 5.09(1H, t, J=5.4 Hz), 4.66(2H, d, J=6.4 Hz), 3.90(3H, s), 3.47(2H, q, J=5.9 Hz), 2.65(2H, t, J=5.9 Hz), 2.57(4H, q, J=7.3 Hz), 2.16–2.02(4H, m), 1.74(3H, s), 1.66(3H, s), 1.59(3H, s), 1.05(6H, t, J=7.3 Hz).

EXAMPLE 30

4-geranyloxy-3-methoxybenzoic acid(1.52 g) was dissolved in chloroform (50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.69 g(84%) of the aimed compound. $^1$H-NMR (CDCl$_3$)δ : 7.45(1H, d, J=2.0 Hz), 7.28(1H, dd, J=2.0 Hz, 8.3 Hz), 7.09(1H, bs), 6.85(1H, d, J=8.3 Hz), 5.50(1H, t, J=6.4 Hz), 5.06(1H, t, J=6.8 Hz), 4.65(2H, d, J=6.4 Hz), 3.91(3H, s), 3.51(2H, q, J=5.9 Hz), 2.70(2H, t, J=5.9 Hz), 2.62(4H, q, J=7.3 Hz), 2.16–2.02(4H, m), 1.73(3H, s), 1.67(3H, s), 1.59(3H, s), 1.07(6H, t, J=7.3 Hz).

EXAMPLE 31

2-geranyloxy-3-methoxybenzoic acid(1.52 g) was dissolved in chloroform (50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.20 g(60%) of the aimed compound.

$^1$H-NMR (CDCl$_3$)δ : 8.36(1H, bs), 7.69(1H, dd, J=1.5 Hz, 7.8 Hz), 7.10(1H, t, J=7.8 Hz), 7.00(1H, dd, J=1.5 Hz, 7.8 Hz), 5.57–5.49(1H, m), 5.08–5.02(1H, m), 4.61(2H, d, J=7.3 Hz), 3.89(3H, s), 3.53(2H, q, J=6.4 Hz), 2.66(2H, t, J=6.4 Hz), 2.60(4H, q, J=7.3 Hz), 2.12–1.98(4H, m), 1.67(3H, s), 1.59(3H, s), 1.04(6H, t, J=7.3 Hz).

EXAMPLE 32

2-geranyloxy-4-methoxybenzoic acid(1.52 g) was dissolved in chloroform (50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.64 g (82%) of the aimed compound.

$^1$H-NMR (CDCl$_3$)δ: 8.24(1H, bs), 8.19(1H, d, J=8.8 Hz), 6.57(1H, dd, J=2.0 Hz, 8.8 Hz), 6.47(1H, d, J=2.4 Hz), 5.55–5.46(1H, m), 5.10–5.02(1H, m), 4.67(2H, d, J=6.4 Hz), 3.83(3H, s), 3.52(2H, q, J=6.4 Hz), 2.63(2H, t, J=6.4 Hz), 2.57(4H, q, J=7.3 Hz), 2.16–2.02(4H, m), 1.75(3H, s), 1.67(3H, s), 1.60(3H, s), 1.03(6H, t, J=7.3 Hz).

EXAMPLE 33

2-geranyloxy-5-methoxybenzoic acid(1.52 g) was dissolved in chloroform (50 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.81 g(90%) of the aimed compound.

$^1$H-NMR (CDCl$_3$)δ: 8.47(1H, bs), 7.77(1H, d, J=3.0 Hz), 7.06–6.82(2H, m), 5.50–5.45(1H, m), 5.08–5.02(1H, m), 4.65(2H, d, J=6.8 Hz), 3.81(3H, s), 3.53(2H, q, J=6.4 Hz), 2.65(2H, t, J=6.4 Hz), 2.58(4H, q, J=7.3 Hz), 2.14–2.02(4H, m), 1.72(3H, s), 1.67(3H, s), 1.60(3H, s), 1.04(6H, t, J=7.3 Hz).

EXAMPLE 34

4-geranyloxy-3-isobutylbenzoic acid(1.85 g) was dissolved in chloroform (37 ml) and triethylamine(1.56 ml), and then diphenylphosphinic chloride(1.0 ml) was added thereto while being cooled with ice. After being stirred for 15 minutes, the mixture, with N,N-diisopropylethylenediamine(0.97 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.78 g(70%) of the aimed compound.

$^1$H-NMR (CDCl$_3$)δ: 7.61(1H, dd, J=2.0 Hz, 8.3 Hz), 7.53 (1H, d, J=2.0 Hz), 7.06–6.82(2H, m), 6.99–6.79(1H, bs), 6.84(1H, d, J=8.8 Hz), 5.53–5.37(1H, m), 5.17–5.02(1H, m), 4.57(2H, d, J=6.4 Hz), 3.50–3.32(2H, m), 3.16–2.98(2H, m), 2.70(2H, t, J=5.9 Hz), 2.50(2H, d, J=7.3 Hz), 2.20–2.00(4H, m), 1.99–1.85(1H, m), 1.72(3H, s), 1.67(3H, s), 1.60(3H, s), 1.05(12H, d, J=6.8 Hz), 0.89(6H, d, J=6.8 Hz).

EXAMPLE 35

2-geranyloxy-5-fluorobenzoic acid(1.46 g) was dissolved in chloroform (40 ml) and triethylamine(1.4 ml), and then diphenylphosphinic chloride(1.0 ml) was added thereto while being cooled with ice. After being stirred for 15 minutes, the mixture, with N,N-diethylethylenediamine(0.7 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 1.62 g(83%) of the aimed compound.
$^1$H-NMR (CDCl$_3$)δ: 8.41(1H, bs), 7.92–7.83(1H, m), 7.10–7.02(1H, m), 6,93–6.85(1H, m), 5.52–5.42(1H, m), 5.13–5.08(1H, m), 4.70(2H, d, J=6.4 Hz), 2.65–2.50(6H, m), 2.15–2.03(4H, m), 1.73(3H, s), 1.66(3H, s), 1.59(3H, s), 1.02(6H, t, J=6.8 Hz).

EXAMPLE 36

4-prenyloxy-3,5-dimethoxybenzoic acid (0.8 g) was dissolved in chloroform (30 ml) and triethylamine(0.44 g), and then diphenylphosphinic chloride(0.80 g) was added thereto while being cooled with ice. After being stirred for 30 minutes, the mixture, with N,N-diethylethylenediamine (0.35 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=8:1), thereby yielding 0.55 g(50%) of the aimed compound.
$^1$H-NMR (CDCl$_3$)δ: 7.04(2H, s), 7.00(1H, s), 5.58–5.51(1H, m), 4.54(2H, d, J=7.3 Hz), 3.89(6H, s), 3.53–3.46(2H, m), 2.74–2.69(4H, m), 2.68–2.57(2H, m), 1.74(3H, s), 1.66(3H, s), 1.08(6H, t, J=6.8 Hz).

EXAMPLE 37

4-geranyloxy-3,5-dimethoxybenzoic acid(1.5 g) was dissolved in chloroform(20 ml) and triethylamine(0.65 g), and then diphenylphosphinic chloride(1.19 g) was added thereto while being cooled with ice. After being stirred for 30 minutes, the mixture, with N,N-diethylethylenediamine (0.52 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=5:1, ethyl acetate:methanol=1:1), thereby yielding 1.44 g(74% of the aimed compound.
$^1$H-NMR (CDCl$_3$)δ: 7.02(2H, s), 5.59–5.50(1H, m), 5.12–5.02(1H, m), 4.57(2H, d, J=6.8 Hz), 3.88(6H, s), 3.52–3.44(2H, m), 2.68(2H, t, J=5.9 Hz), 2.64–2.55(4H, m), 2.07–1.91(4H, m), 1.67(3H, s), 1.64(3H, s), 1.58(3H, s), 1.06(6H, t, J=6.8 Hz).

EXAMPLE 38

In a manner identical to Example 37, 4-neryloxy-3,5-dimethoxybenzoic acid was subjected to a condensation reaction with N,N-diethylethylenediamine, thereby yielding the aimed compound.

EXAMPLE 39

3-geranyloxy-4,5-dimethoxybenzoic acid(0.7 g) was dissolved in chloroform(30 ml) and triethylamine(0.31 g), and then diphenylphosphinic chloride (0.56 g) was added thereto while being cooled with ice. After being stirred for 30 minutes, the mixture, with N,N-diethylethylenediamine (0.24 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=8:1), thereby yielding 0.86 g(95%) of the aimed compound.
$^1$H-NMR (CDCl$_3$)δ: 7.04(2H, s), 6.95(1H, s), 5.55–5.48(1H, m), 5.12–5.02(1H, m), 4.63(2H, d, J=6.4 Hz), 3.89(3H, s), 3.88(3H, s), 3.52–3.42(2H, m), 2.75–2.67(2H, m), 2.66–2.54(4H, m), 2.12–2.05(4H, m), 1.73(3H, s), 1.66(3H, s), 1.59(3H, s), 1.07(6H, t, J=6.8 Hz).

EXAMPLE 40

3-prenyloxy-4,5-dimethoxybenzoic acid(0.8 g) was dissolved in chloroform(30 ml) and triethylamine(0.44 g), and then diphenylphosphinic chloride (0.80 g) was added thereto while being cooled with ice. After being stirred for 30 minutes, the mixture, with N,N-diethylethylenediamine (0.35 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 0.65 g(59%) of the aimed compound.
$^1$H-NMR (CDCl$_3$)δ: 7.05(2H, s), 6.97(1H, s), 5.55–5.47(1H, m), 4.61(2H, d, J=6.4 Hz), 3.90(3H, s), 3.89(3H, s), 3.52–3.45(2H, m), 2.72–2.67(2H, m), 2.66–2.55(4H, m), 1.78(3H, s), 1.75(3H, s), 1.08(6H, t, J=6.8 Hz).

EXAMPLE 41

4-prenyloxy-3,5-dimethoxybenzoic acid(1.0 g) was dissolved in chloroform(30 ml) and triethylamine(0.55 g), and then diphenylphosphinic chloride (1.0 g) was added thereto while being cooled with ice. After being stirred for 30 minutes, the mixture, with N,N-dimethylethylenediamine (0.33 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=5:1), thereby yielding 0.93 g(74%) of the aimed compound.

EXAMPLE 42

3-geranyloxy-4,5-dimethoxybenzoic acid(0.7 g) was dissolved in chloroform(30 ml) and triethylamine(0.31 g), and then diphenylphosphinic chloride (0.56 g) was added thereto while being cooled with ice. After being stirred for 30 minutes, the mixture, with N,N-dimethylethylenediamine (0.19 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=12:1), thereby yielding 0.85 g(100%) of the aimed compound.

EXAMPLE 43

4-geranyloxy-3,5-dimethoxybenzoic acid(0.8 g) was dissolved in chloroform(25 ml) and triethylamine(0.35 g), and then diphenylphosphinic chloride (0.69 g) was added thereto while being cooled with ice. After being stirred for 30 minutes, the mixture, with N,N-dimethylethylenediamine (0.21 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=5:1), thereby yielding 0.83 g(86%) of the aimed compound.
m.p. 49–55° C.
$^1$H-NMR (CDCl$_3$)δ: 7.02(2H, s), 6.72(1H, s), 5.60–5.50(1H, m), 5.12–5.04(1H, m), 4.58(2H, d, J=6.8 Hz), 3.90(6H, s), 3.57–3.49(2H, m), 2.58–2.50(2H, m), 2.29(6H, s), 2.13–1.94(4H, m), 1.67(3H, s), 1.66(3H, s), 1.60(3H, s).

EXAMPLE 44

6-prenyloxynicotinic acid(1.0 g) was dissolved in chloroform(30 ml) and triethylamine(0.71 g), and then diphenylphosphinic chloride(1.28 g) was added thereto while being cooled with ice. After being stirred for 30 minutes, the mixture, with N,N-dimethylethylenediamine (0.43 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=3:1), thereby yielding 1.23 g(92%) of the aimed compound.

EXAMPLE 45

2-prenyloxynicotinic acid(1.2 g) was dissolved in chloroform(30 ml) and triethylamine(0.85 g), and then diphenylphosphinic chloride(1.54 g) was added thereto while being cooled with ice. After being stirred for 30 minutes, the mixture, with N,N-dimethylethylenediamine (0.51 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 1.46 g(91%) of the aimed compound.

EXAMPLE 46

6-prenyloxynicotinic acid(0.7 g) was dissolved in chloroform(30 ml) and triethylamine(0.49 g), and then diphenylphosphinic chloride(0.98 g) was added thereto while being cooled with ice. After being stirred for 30 minutes, the mixture, with N,N-diethylethylenediamine (0.39 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=4:1), thereby yielding 0.75 g of the aimed compound.
$^1$H-NMR (CDCl$_3$)δ: 8.08(1H, d, J=2.4 Hz), 7.60–7.50(1H, m), 6.77(1H, s), 6.52(1H, d, J=9.3 Hz), 5.35–5.25(1H, m), 4.56(2H, d, J=7.3 Hz), 3.50–3.38(2H, m), 2.64–2.53(2H, m), 1.78(6H, s), 1.03(6H, d, J=6.8 Hz).

EXAMPLE 47

2-prenyloxynicotinic acid(1.0 g) was dissolved in chloroform(30 ml) and triethylamine(0.71 g), and then diphenylphosphinic chloride(1.40 g) was added thereto while being cooled with ice. After being stirred for 30 minutes, the mixture, with N,N-diethylethylenediamine (0.56 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 0.57 g(39%) of the aimed compound.
$^1$H-NMR (CDCl$_3$)δ: 9.88(1H, s), 8.45–8.51(1H, m), 7.52–7.47(1H, m), 6.37(1H, t, J=6.8 Hz), 5.33–5.26(1H, m), 4.61(2H, d, J=6.8 Hz), 3.59–3.50(2H, m), 2.75–2.69(2H, m), 2.68–2.57(4H, m), 1.80(3H, s), 1.79(3H, s), 1.07(6H, d, J=7.3 Hz).

EXAMPLE 48

6-prenyloxynicotinic acid(1.57 g) was dissolved in tetrahydrofuran (32 ml), and then N,N'-carbonyldiimidazole (1.35 g) was added thereto while being cooled with ice. After being stirred for 1.5 hours, the mixture, with N,N-diisopropyl ethylenediamine (1.32 ml) added thereto, was stirred for one night at room temperature. The reaction mixture was concentrated under a vacuum, and the residue, with saturated sodium hydrogencarbonate aqueous solution (60 ml) added thereto, was extracted with ethyl acetate. The extract was washed with water and saturated brine successively, dried over sodium sulfate anhydride, and then concentrated under a vacuum. The residue was purified by silica gel column chromatography (chloroform:methanol= 20:1), thereby yielding 1.26 g(50%) of the aimed compound.
$^1$H-NMR (CDCl$_3$)δ: 8.09(1H, d, J=2.4 Hz), 7.54(1H, dd, J=2.4 Hz, 9.8 Hz), 6.80–6.90(1H, bs), 6.54(1H, d, J=9.8 Hz), 5.27–5.33(1H, m), 4.57(2H, d, J=7.3 Hz), 3.36(2H, q, J=5.9 Hz), 3.06(2H, q, J=5.9 Hz), 3.06(2H, quint., J=6.8 Hz), 2.68(2H, t, J=5.9 Hz), 1.78(6H, s), 1.04(12H, d, J=6.8 Hz).

EXAMPLE 49

6-prenyloxynicotinic acid(0.9 g) was dissolved in chloroform(30 ml) and triethylamine(0.48 g), and then diphenylphosphinic chloride(0.87 g) was added thereto while being cooled with ice. After being stirred for 30 minutes, the mixture, with N,N-dimethylethylenediamine (0.29 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=3:1), thereby yielding 1.11 g(98%) of the aimed compound.

EXAMPLE 50

6-geranyloxynicotinic acid(0.8 g) was dissolved in chloroform(30 ml) and triethylamine(0.34 g), and then diphenylphosphinic chloride(0.84 g) was added thereto while being cooled with ice. After being stirred for 30 minutes, the mixture, with N,N-diethylethylenediamine (0.43 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=6:1), thereby yielding 0.79 g(73%) of the aimed compound.

$^1$H-NMR (CDCl$_3$)δ: 8.08(1H, d, J=2.4 Hz), 7.57–7.50(1H, m), 6.74(1H, s), 6.53(1H, d, J=9.8 Hz), 5.34–5.26(1H, m), 5.10–5.00(1H, m), 4.59(2H, d, J=6.8 Hz), 3.48–3.38(2H, m), 2.70–2.47(6H, m), 2.16–2.00(4H, m), 1.78(3H, s), 1.66(3H, s), 1.58(3H, s), 1.04(6H, d, J=7.3 Hz).

EXAMPLE 51

6-geranyloxynicotinic acid(1.40 g) was dissolved in tetrahydrofuran (30 ml), and then N,N'-carbonyldiimidazole (0.92 g) was added thereto while being cooled with ice. After being stirred for 1.5 hours, the mixture, with N,N-diisopropyl ethylenediamine (0.88 ml) added thereto, was stirred for one night at room temperature. The reaction mixture was concentrated under a vacuum, and the result, with saturated sodium hydrogencarbonate aqueous solution (60 ml) added thereto, was extracted with ethyl acetate. The extract was washed with water and saturated brine successively, dried over sodium sulfate anhydride, and then concentrated under a vacuum. The residue was purified by silica gel column chromatography (chloroform:methanol= 20:1), thereby yielding 1.29 g(63%) of the aimed compound.

EXAMPLE 52

2-geranyloxynicotinic acid(0.8 g) was dissolved in chloroform(40 ml) and triethylamine(0.43 g), and then diphenylphosphinic chloride(0.77 g) was added thereto while being cooled with ice. After being stirred for 30 minutes, the mixture, with N,N-diethylethylenediamine (0.34 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 0.91 g(84%) of the aimed compound.
$^1$H-NMR (CDCl$_3$)δ: 9.58(1H, s), 8.53–8.46(1H, m), 7.53–7.46(1H, m), 6.41–6.32(1H, m), 5.33–5.20(1H, m), 5.10–5.02(1H, m), 4.62(2H, d, J=7.3 Hz), 3.60–3.50(2H, m), 2.75–2.69(2H, m), 2.68–2.57(4H, m), 2.11(6H, s), 1.77(3H, s), 1.67(3H, s), 1.59(3H, s), 1.07(6H, t, J=7.3 Hz).

EXAMPLE 53

In a manner identical to Example 54, 3-prenyloxypicolinic acid was subjected to a condensation reaction with N,N-dimethylethylenediamine, thereby yielding the aimed compound.

EXAMPLE 54

3-prenyloxypicolinic acid(1.0 g) was dissolved in chloroform(30 ml) and triethylamine(0.71 g), and then diphenylphosphinic chloride(1.28 g) was added thereto while being cooled with ice. After being stirred for 30 minutes, the mixture, with N,N-diethylethylenediamine (0.56 g) added thereto, was stirred for 4 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=3.5:1), thereby yielding 0.87 g(59%) of the aimed compound.

EXAMPLE 55

3-prenyloxypicolinic acid(1.80 g) was dissolved in tetrahydrofuran (36 ml), and then N,N'-carbonyldiimidazole (1.58 g) was added thereto while being cooled with ice. After being stirred for 1.5 hours, the mixture, with N,N-diisopropyl ethylenediamine (1.54 ml) added thereto, was stirred for one night at room temperature. The reaction mixture was concentrated under a vacuum, and the result, with saturated sodium hydrogencarbonate aqueous solution (60 ml) added thereto, was extracted with ethyl acetate. The extract was washed with water and saturated brine successively, dried over sodium sulfate anhydride, and then concentrated under a vacuum. The residue was purified by silica gel column chromatography (chloroform:methanol= 25:1), thereby yielding 1.58 g(55%) of the aimed compound.

EXAMPLE 56

3-benzyloxy-4-isobutylbenzoic acid(2.00 g) was suspended in ethyl acetate, and then triethylamine(0.71 g) was added thereto. While being cooled to −10° C., ethyl chloroacetate(0.7 ml) was gradually added to the mixture. After being stirred for 30 minutes, the mixture, with N,N-diethylethylenediamine(0.81 g) added thereto, was stirred for 3 hours at room temperature. The solids in the reaction mixture was filtrated out, and the filtrate was washed with saturated sodium hydrogencarbonate aqueous solution, dried over sodium sulfate anhydride, and then concentrated under a vacuum. The resulting amide was dissolved in a mixture of ethanol and ethyl acetate, and the solution, with 10% palladium-carbon(0.50 g) added thereto, was stirred for 4.5 hours at room temperature in a hydrogen gas atmosphere. The reaction mixture was filtrated, and the filtrate was concentrated. The concentrate was washed with saturated sodium hydrogencarbonate aqueous solution and saturated brine successively, dried over sodium sulfate anhydride, and then concentrated under a vacuum. The resulting solids were recrystallized from a mixture of hexane and ethyl acetate, thereby yielding 1.00 g of the aimed compound as colorless crystals.
m.p. 108–109° C.
$^1$H-NMR (CDCl$_3$)δ: 7.51–7.07(3H, m), 6.99(1H, m), 3.50 (2H, m), 2.67(2H, t), 2.52(2H, d), 1.97(1H, m), 1.05(6H, t), 0.92(6H, d).

EXAMPLE 57

4-(4-fluorobenzyloxy)-3-isobutylbenzoic acid(1.90 g) was dissolved in chloroform(35 ml) and triethylamine(1.75 ml), and then diphenylphosphinic chloride(1.20 ml) was added thereto while being cooled with ice. After being stirred for 15 minutes, the mixture, with N,N-diisopropylethylenediamine(1.09 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 1.50 g(56%) of the aimed compound.
$^1$H-NMR (CDCl$_3$)δ: 7.62(1H, dd, J=2.0 Hz, 8.8 Hz), 7.56 (1H, d, J=2.0 Hz), 7.40(1H, d, J=8.8 Hz), 7.38(1H, d, J=8.8 Hz), 7.09(1H, d, J=8.8 Hz), 7.07(1H, d, J=8.8 Hz), 6.89(1H, d, J=8.8 Hz), 6.95–6.84(1H, bs), 5.06(2H, s), 3,40(2H, q, J=5.9 Hz), 3.15–2.99(2H, m), 2,70(2H, t, J=5.9 Hz), 2.54 (2H, d, J=6.8 Hz), 2.07–1.94(1H, m), 1.04(12H, d, J=6.8 Hz), 0.90(6H, d, J=6.4 Hz).

EXAMPLE 58

3,4-methylenedioxybenzoic acid(1.52 g) was dissolved in chloroform(30 ml) and triethylamine(2.6 ml), and then diphenylphosphinic chloride(1.77 ml) was added thereto while being cooled with ice. After being stirred for 15 minutes, the mixture, with N,N-diisopropylethylenediamine (1.70 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 1.51 g(56%) of the aimed compound.

$^1$H-NMR (CDCl$_3$)δ: 7.60(1H, dd, J=2.0 Hz, 7.8 Hz), 7.28 (1H, s), 6.95–6.77(1H, bs), 6.82(1H, d, J=7.8 Hz), 6.01(2H, s), 3.39(2H, q, J=5.9 Hz), 3.13–2.99(2H, m), 2.67(2H, t, J=5.9 Hz), 1.04(12H, d, J=6.8 Hz).

EXAMPLE 59

4-isopropoxybenzoic acid(1.61 g) was dissolved in chloroform(30 ml) and triethylamine(2.5 ml), and then diphenylphosphinic chloride(1.73 ml) was added thereto while being cooled with ice. After being stirred for 15 minutes, the mixture, with N,N-diisopropylethylenediamine (1.57 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=12:1), thereby yielding 1.49 g(55%) of the aimed compound.

$^1$H-NMR (CDCl$_3$)δ: 7.72(2H, d, J=8.8 Hz), 6.88(2H, d, J=8.8 Hz), 4.65–4.54(1H, m), 3.46–3.38(2H, m), 3.15–3.02 (2H, m), 2.80–2.65(2H, m), 1.69(6H, d, J=5.9 Hz), 1.05 (12H, d, J=6.8 Hz).

EXAMPLE 60

4-isobutoxybenzoic acid(1.73 g) was dissolved in chloroform(35 ml) and triethylamine(2.5 ml), and then diphenylphosphinic chloride(1.72 ml) was added thereto while being cooled with ice. After being stirred for 15 minutes, the mixture, with N,N-diisopropylethylenediamine (1.56 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 1.93 g(68%) of the aimed compound.

$^1$H-NMR (CDCl$_3$)δ: 7.73(2H, d, J=8.8 Hz), 6.90(2H, d, J=8.8 Hz), 6.84–6.98(1H, bs), 3.75(2H, d, J=6.4 Hz), 3.40 (2H, q, J=5.9 Hz), 2.99–3.13(2H, m), 2.69(2H, t, J=5.9 Hz), 2.01–2.17(1H, m), 1.04(12H, d, J=6.4 Hz), 1.02(6H, d, J=6.4 Hz).

EXAMPLE 61

4-tert-butylbenzoic acid(1.66 g) was dissolved in chloroform(33 ml) and triethylamine(2.60 ml), and then diphenylphosphinic chloride(1.80 ml) was added thereto while being cooled with ice. After being stirred for 15 minutes, the mixture, with N,N-diisopropylethylenediamine (1.64 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=15:1), thereby yielding 2.37 g(83%) of the aimed compound.

$^1$H-NMR (CDCl$_3$)δ: 7.71(2H, d, J=8.3 Hz), 7.44(2H, d, J=8.3 Hz), 7.02–6.82(1H, bs), 3.42(2H, q, J=5.9 Hz), 3.14–3.00(2H, m), 2.70(2H, t, J=5.9 Hz), 1.33(9H, s), 1.05 (12H, d, J=6.3 Hz).

EXAMPLE 62

4-pentylbenzoic acid(1.81 g) was dissolved in chloroform (35 ml) and triethylamine(2.62 ml), and then diphenylphosphinic chloride(1.80 ml) was added thereto while being cooled with ice. After being stirred for 15 minutes, the mixture, with N,N-diisopropylethylenediamine(1.65 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 20:1), thereby yielding 1.98 g(66%) of the aimed compound.

$^1$H-NMR (CDCl$_3$)δ: 7.70(2H, d, J=8.3 Hz), 7.22(2H, d, J=8.3 Hz), 6.92–7.02(1H, bs), 3.42(2H, q, J=5.9 Hz), 2.99–3.13(2H, m), 2.69(2H, t, J=5.9 Hz), 2.63(2H, t, J=7.8 Hz), 1.56–1.68(2H, m), 1.26–1.38(4H, m), 1.04(12H, d, J=6.8 Hz), 0.89(3H, t, J=6.8 Hz).

EXAMPLE 63

4-octylbenzoic acid(1.91 g) was dissolved in chloroform (35 ml) and triethylamine(2.3 ml), and then diphenylphosphinic chloride(1.56 ml) was added thereto while being cooled with ice. After being stirred for 15 minutes, the mixture, with N,N-diisopropylethylenediamine(1.43 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol= 15:1), thereby yielding 2.53 g(86%) of the aimed compound.

$^1$H-NMR (CDCl$_3$)δ: 7.69(2H, d, J=7.8 Hz), 7.22(2H, d, J=7.8 Hz), 7.04–6.89(1H, bs), 3.42(2H, q, J=5.4 Hz), 3.13–2.99(2H, m), 2.70(2H, t, J=5.9 Hz), 2.63(2H, t, J=7.8 Hz, 1.67–1.56(2H, m), 1.39–1.16(10H, m), 1.09(12H, d, J=6.8 Hz), 0.88(3H, t, J=7.3 Hz).

EXAMPLE 64

4-isopropylbenzoic acid(1.69 g) was dissolved in chloroform(33 ml) and triethylamine(2.90 ml), and then diphenylphosphinic chloride(1.97 ml) was added thereto while being cooled with ice. After being stirred for 15 minutes, the mixture, with N,N-diisopropylethylenediamine (1.80 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=20:1), thereby yielding 2.06 g(69%) of the aimed compound.

$^1$H-NMR (CDCl$_3$)δ: 7.71(2H, d, J=8.3 Hz), 7.28(2H, d, J=8.3 Hz), 7.03–6.90(1H, bs), 3.42(2H, q, J=5.9 Hz), 3.14–3.00(2H, m), 3.00–2.88(1H, m), 2.70(2H, t, J=5.9 Hz), 1.26(6H, d, J=6.8 Hz), 1.04(12H, d, J=6.4 Hz).

EXAMPLE 65

3,5-di-tert-butylbenzoic acid(1.71 g) was dissolved in chloroform(35 ml) and triethylamine(2.05 ml), and then diphenylphosphinic chloride(1.40 ml) was added thereto while being cooled with ice. After being stirred for 15 minutes, the mixture, with N,N-diisopropylethylenediamine (1.28 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The resulting crystals were recrystallized from ethyl acetate with hexane, thereby yielding 2.44 g(93%) of the aimed compound as white crystals.

m.p. 159.0–160.6° C.

$^1$H-NMR (CDCl$_3$)δ: 7.63(2H, d, J=1.5 Hz), 7.55(1H, t, J=1.5 Hz), 7.04–6.92(1H, bs), 3.42(2H, q, J=5.9 Hz), 3.16–3.00 (2H, m), 2.72(2H, t, J=5.9 Hz),1.34(18H, s), 1.06(12H, d, J=6.8 Hz).

EXAMPLE 66

3-piperidinomethylbenzoic acid(1.70 g) was dissolved in chloroform(35 ml) and triethylamine(2.16 ml), and then diphenylphosphinic chloride(1.48 ml) was added thereto while being cooled with ice. After being stirred for 15 minutes, the mixture, with N,N-diisopropylethylenediamine (1.35 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=8:1), thereby yielding 1.48 g(55%) of the aimed compound.

$^1$H-NMR (CDCl$_3$)δ: 7.74(1H, s), 7.66(1H, d, J=7.8 Hz), 7.44(1H, d, J=7.8 Hz), 7.36(1H, t, J=7.8 Hz), 7.09–6.94(1H, bs), 3.49(2H, s), 3.42(2H, q, J=5.9 Hz), 3.14–3.00(2H, m), 2.71(2H, t, J=5.9 Hz), 2.45–2.28(4H, bs), 1.62–1.50(4H, m), 1.48–1.37(2H, m), 1.05(12H, d, J=6.8 Hz).

EXAMPLE 67

4-(tert-butylcarbamoyl)benzoic acid(1.78 g) was dissolved in chloroform (35 ml) and triethylamine(2.5 ml), and then diphenylphosphinic chloride(1.54 g) was added thereto while being cooled with ice. After being stirred for 15 minutes, the mixture, with N,N-diisopropylethylenediamine (1.44 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The resulting crystals were recrystallized from chloroform with hexane, thereby yielding 2.41 g(86%) of the aimed compound as white crystals.

m.p. 187.6–188.5° C.

$^1$H-NMR (CDCl$_3$)δ: 7.80(2H, d, J=8.3 Hz), 7.77(2H, d, J=8.5 Hz), 7.10–6.92(1H, bs), 6.06–5.90(1H, bs), 3.42(2H, q, J=5.9 Hz), 3.13–2.99(2H, m), 2.71(2H, t, J=5.9 Hz), 1.48(9H, s), 1.04(12H, d, J=6.4 Hz).

EXAMPLE 68

4-tert-butylaminobenzoic acid(1.59 g) was dissolved in chloroform(32 ml) and triethylamine(2.3 ml), and then diphenylphosphinic chloride(1.58 ml) was added thereto while being cooled with ice. After being stirred for 15 minutes, the mixture, with N,N-diisopropylethylenediamine (1.45 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=12:1), thereby yielding 1.46 g(56%) of the aimed compound.

$^1$H-NMR (CDCl$_3$)δ: 7.59(2H, d, J=8.8 Hz), 6.87–6.68(1H, bs), 6.66(2H, d, J=8.8 Hz), 3.60–4.28(1H, bs), 3.40(2H, q, J=5.4 Hz), 3.15–2.98(2H, m), 2.68(2H, t, J=5.9 Hz), 1.39 (9H, s), 1.04(12H, d, J=6.8 Hz).

EXAMPLE 69

4-pivaloylaminobenzoic acid(1.71 g) was dissolved in chloroform(35 ml) and triethylamine(2.15 ml), and then diphenylphosphinic chloride(1.48 ml) was added thereto while being cooled with ice. After being stirred for 15 minutes, the mixture, with N,N-diisopropylethylenediamine (1.36 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The resulting crystals were recrystallized from chloroform and methanol with hexane, thereby yielding 2.32 g(86%) of the aimed compound as white crystals.

m.p. 200.1–200.8° C.

$^1$H-NMR (CDCl$_3$)δ: 7.74(2H, d, J=8.8 Hz), 7.62(2H, d, J=8.8 Hz), 7.59–7.47(1H, bs), 7.00–6.86(1H, bt), 3.40(2H, q, J=5.9 Hz), 3.12–2.99(2H, m), 2.69(2H, t, J=5.9 Hz), 1.32(9H, s), 1.03(12H, d, J=6.8 Hz).

EXAMPLE 70

4-dimethylaminobenzoic acid(1.51 g) was dissolved in chloroform(30 ml) and triethylamine(2.55 ml), and then diphenylphosphinic chloride(1.76 ml) was added thereto while being cooled with ice. After being stirred for 15 minutes, the mixture, with N,N-diisopropylethylenediamine (1.60 ml) added thereto, was stirred for 1.5 hours at room temperature. The reaction mixture was washed with saturated sodium hydrogencarbonate aqueous solution and saturated brine successively, dried over sodium sulfate anhydride, and then concentrated under a vacuum. The residue was purified by silica gel column chromatography (chloroform:methanol=10:1), thereby yielding 0.99 g(37%) of the aimed compound.

$^1$H-NMR (CDCl$_3$)δ: 7.68(2H, d, J=8.8 Hz), 6.72–6.86(1H, bs), 6.68(2H, d, J=8.8 Hz), 3.41(2H, q, J=5.9 Hz), 3.14–2.99 (2H, m), 3.01(6H, s), 2.69(2H, t, J=5.9 Hz), 1.04(12H, d, J=6.8 Hz).

What is claimed is:

1. An alkylenediamine compound or a salt thereof expressed by the following formula 6:

formula 6

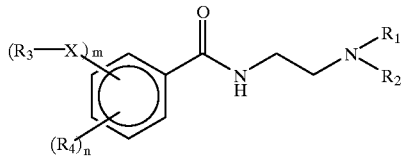

Wherein each of $R_1$ and $R_2$ represents a lower alkyl group; $R_3$ is an unsaturated aliphatic hydrocarbon having at least one double bond; $R_4$ is a lower alkyl group, a lower alkoxy group, or a halogen atom; X is a group expressed by —O—, —S—, or —N($R_5$)—, while $R_5$ is hydrogen atom, a lower alkyl group, or an unsaturated aliphatic hydrocarbon having at least one double bond; m is an integer of 1 to 3; and n is an integer of 0 to 2, wherein when X is —O—, m is an integer of 2 to 3.

2. An alkylenediamine compound or a salt thereof expressed by the following formula 6:

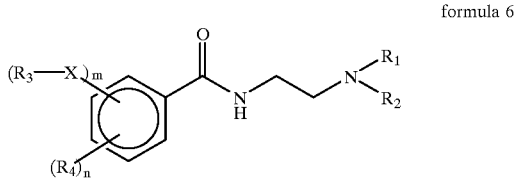

formula 6 wherein each of $R_1$ and $R_2$ represents a lower alkyl group; $R_3$ is an unsaturated aliphatic hydrocarbon having at least one double bond; $R_4$ is a lower alkyl group, a lower alkoxy group, or a halogen atom; X is a group expressed by —O—, —S—, or —N($R_5$)—, while $R_5$ is hydrogen atom, a lower alkyl group, or an unsaturated aliphatic hydrocarbon having at least one double bond; m is an integer of 1 to 3; and n is an integer of 1 or 2, wherein when X is —O—, at least one $R_4$ is an alkoxy group.

3. An alkylenediamine compound or a salt thereof according to claim 2, wherein $R_4$ is a lower alkoxy group.

4. An alkylenediamine compound or a salt thereof according to claim 1, wherein $R_3$ is prenyl, geranyl, neryl or farnesyl group.

5. An alkylenediamine compound or a salt thereof according to claim 1, wherein X is —O—.

6. An alkylenediamine compound or a salt thereof according to claim 1, wherein $R_1$ and $R_2$ are ethyl or isopropyl groups.

7. An alkylenediamine compound or a salt thereof according to claim 2, wherein $R_3$ is prenyl, geranyl, neryl or farnesyl group.

8. An alkylenediamine compound or a salt thereof according to claim 2, wherein X is —O—.

9. An alkylenediamine compound or a salt thereof according to claim 2, wherein $R_1$ and $R_2$ are ethyl or isopropyl groups.

10. An alkylenediamine compound or a salt thereof expressed by the following formula 6:

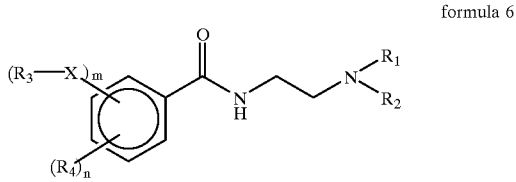

formula 6 wherein each of $R_1$ and $R_2$ represents a lower alkyl group; $R_3$ is geranyl, neryl, or farnesyl; $R_4$ is a lower alkyl group or a halogen atom; X is a group expressed by —O—, —S—, or —N($R_5$)—, while $R_5$ is hydrogen atom, a lower alkyl group, or an unsaturated aliphatic hydrocarbon having at least one double bond; m is 1; and n is 0 or 1.

11. An alkylenediamine compound or a salt thereof according to claim 10, wherein X is —O—.

12. An alkylenediamine compound or a salt thereof according to claim 10, wherein n is 0.

13. An alkylenediamine compound or a salt thereof according to claim 10, wherein n is 1 and $R_4$ is a lower alkyl group.

14. An anti-ulcer composition comprising, as an effective ingredient, an alkylenediamine compound or a pharmacologically acceptable salt thereof according to claim 1, together with a pharmaceutically acceptable carrier and/or adjuvant.

15. An antibacterial composition against *Helicobacter pyroli* comprising, as an effective ingredient, an alkylenediamine compound or a pharmacologically acceptable salt thereof according to claim 1, together with a pharmaceutically acceptable carrier and/or adjuvant.

16. An anti-ulcer composition comprising, as an effective ingredient, an alkylenediamine compound or a pharmacologically acceptable salt thereof according to claim 2, together with a pharmaceutically acceptable carrier and/or adjuvant.

17. An antibacterial composition against *Helicobacter pyroli* comprising, as an effective ingredient, an alkylenediamine compound or a pharmacologically acceptable salt thereof according to claim 2, together with a pharmaceutically acceptable carrier and/or adjuvant.

18. An anti-ulcer composition comprising, as an effective ingredient, an alkylenediamine compound or a pharmacologically acceptable salt thereof according to claim 10, together with a pharmaceutically acceptable carrier and/or adjuvant.

19. An antibacterial composition against *Helicobacter pyroli* comprising, as an effective ingredient, an alkylenediamine compound or a pharmacologically acceptable salt thereof according to claim 10, together with a pharmaceutically acceptable carrier and/or adjuvant.

20. A method for the treatment of peptic ulcers in man or mammals, which comprises administering an effective amount of an alkylenediamine compound or a pharmacologically acceptable salt thereof according to claim 1 to a host.

21. A method according to claim 20, wherein said peptic ulcers are gastric ulcers in man.

22. A method for the inhibition of acid secretion in stomach of man or mammals, which comprises administering an effective amount of an alkylenediamine compound or a pharmacologically acceptable salt thereof according to claim 1 to a host.

23. A method for the inhibition of growth if *Helicobacter pyroli* in stomach of man or mammals, which comprises administering an effective amount of an alkylenediamine compound or a pharmacologically acceptable salt thereof according to claim 1 to a host.

24. A method for the prevention of peptic ulcers in man or mammals, which comprises administering an effective amount of an alkylenediamine compound or a pharmacologically acceptable salt thereof according to claim 1 to a host.

25. A method according to claim 24, wherein said peptic ulcers are gastric ulcers in man.

26. A method for the treatment of peptic ulcers in man or mammals, which comprises administering an effective amount of an alkylenediamine compound or a pharmacologically acceptable salt thereof according to claim 2 to a host.

27. A method according to claim 26, wherein said peptic ulcers are gastric ulcers in man.

28. A method for the inhibition of acid secretion in stomach of man or mammals, which comprises administering an effective amount of an alkylenediamine compound or a pharmacologically acceptable salt thereof according to claim 2 to a host.

29. A method for the inhibition of growth of *Helicobacter pyroli* in stomach of man or mammals, which comprises administering an effective amount of an alkylenediamine compound or a pharmacologically acceptable salt thereof according to claim 2 to a host.

30. A method for the prevention of peptic ulcers in man or mammals, which comprises administering an effective amount of an alkylenediamine compound or a pharmacologically acceptable salt thereof according to claim 2 to a host.

31. A method according to claim 30, wherein said peptic ulcers are gastric ulcers in man.

32. An alkylenediamine compound or a salt thereof according to claim 1, wherein n is 0.

33. A method for the treatment of peptic ulcers in man or mammals, which comprises administering an effective amount of an alkylenediamine compound or a pharmacologically acceptable salt thereof according to claim 10 to a host.

34. A method according to claim 33, wherein said peptic ulcers are gastric ulcers in man.

35. A method for the inhibition of acid secretion in stomach of man or mammals, which comprises administering an effective amount of an alkylenediamine compound or a pharmacologically acceptable salt thereof according to claim 10 to a host.

36. A method for the inhibition of growth of *Helicobacter pyroli* in stomach of man or mammals, which comprises administering an effective amount of an alkylenediamine compound or a pharmacologically acceptable salt thereof according to claim 10 to a host.

37. A method for the prevention of peptic ulcers in man or mammals, which comprises administering an effective amount of an alkylenediamine compound or a pharmacologically acceptable salt thereof according to claim 10 to a host.

38. A method according to claim 37, wherein said peptic ulcers are gastric ulcers in man.

\* \* \* \* \*